(12) United States Patent
Takis et al.

(10) Patent No.: US 10,401,312 B2
(45) Date of Patent: Sep. 3, 2019

(54) METHOD FOR PREDICTING CHEMICAL SHIFT VALUES OF NMR SPIN SYSTEMS IN A SAMPLE OF A FLUID CLASS, IN PARTICULAR IN A SAMPLE OF A BIOFLUID

(71) Applicant: Bruker BioSpin GmbH, Rheinstetten (DE)

(72) Inventors: Panteleimon Takis, Sesto Fiorentino (IT); Claudio Luchinat, Florence (IT)

(73) Assignee: BRUKER BIOSPIN GMBH, Rheinstetten (DE)

( * ) Notice: Subject to any disclaimer, the term of this patent is extended or adjusted under 35 U.S.C. 154(b) by 170 days.

(21) Appl. No.: 15/622,896

(22) Filed: Jun. 14, 2017

(65) Prior Publication Data

US 2017/0356865 A1 Dec. 14, 2017

(30) Foreign Application Priority Data

Jun. 14, 2016 (EP) .................................... 16174410

(51) Int. Cl.
*G01N 24/08* (2006.01)
*G01R 33/46* (2006.01)
*G01R 33/465* (2006.01)

(52) U.S. Cl.
CPC ........... *G01N 24/08* (2013.01); *G01R 33/465* (2013.01); *G01R 33/4625* (2013.01)

(58) Field of Classification Search
USPC .................................................. 324/300–322
See application file for complete search history.

(56) References Cited

U.S. PATENT DOCUMENTS

| 4,933,844 A | 6/1990 | Otvos et al. |
| 6,278,893 B1 | 8/2001 | Ardenkjaer-Larson et al. |

(Continued)

FOREIGN PATENT DOCUMENTS

| CN | 1527066 A | 12/1998 |
| CN | 102435474 A | 5/2012 |

(Continued)

OTHER PUBLICATIONS

Holmes, E. et al., "Human metabolic phenotype diversity and its association with diet and blood pressure." Nature 453, 2008, pp. 396-400.

(Continued)

*Primary Examiner* — Jay Patidar
(74) *Attorney, Agent, or Firm* — Edell, Shapiro & Finnan, LLC

(57) ABSTRACT

Correlation information between captured characteristics and chemical shift values of captured NMR spin systems is provided by a model appliance for a fluid class. An NMR spectrum of a sample of the fluid class is recorded. Peaks in the recorded NMR spectrum which belong to defined reference NMR spin systems are identified, and experimental chemical shift values of the peaks from the recorded NMR spectrum are determined. A chemical shift value of at least one of the captured NMR spin systems not belonging to the reference NMR spin systems is predicted by applying the model appliance onto the experimental chemical shift values of the reference NMR spin systems. Peaks in an NMR spectrum of a sample of a fluid class are attributed more quickly and reliably to NMR spins systems of compounds contained in the sample.

24 Claims, 12 Drawing Sheets

(56) References Cited

U.S. PATENT DOCUMENTS

| | | | |
|---|---|---|---|
| 7,191,069 | B2 | 3/2007 | Wishart et al. |
| 9,470,771 | B2 | 10/2016 | Otvos et al. |
| 2002/0173920 | A1 | 11/2002 | Xu et al. |
| 2012/0197539 | A1* | 8/2012 | Slupsky .................. G01N 24/08 702/19 |
| 2015/0042328 | A1 | 2/2015 | Huber et al. |
| 2015/0099668 | A1 | 4/2015 | Farshidfar et al. |
| 2015/0149094 | A1* | 5/2015 | Otvos .................. G01R 33/465 702/19 |

FOREIGN PATENT DOCUMENTS

| | | |
|---|---|---|
| CN | 104508471 A | 4/2015 |
| EP | 0361214 A1 | 4/1990 |
| EP | 3015855 A1 | 5/2016 |
| GB | 2341685 A | 3/2003 |
| JP | H02-223877 A | 9/1990 |
| JP | H08-252238 A | 10/1996 |
| JP | 2005-161102 A | 6/2005 |
| JP | 2005312821 A | 11/2005 |
| JP | 2015-512520 A | 4/2015 |

OTHER PUBLICATIONS

Weckwerth, W. et al., "Differential metabolic networks unravel the effects of silent plant phenotypes." Proc. Natl. Acad. Sci. United States Am., 101, 2004, pp. 7809-7814, Larive, C.K. et al., "Spectroscopy for Metabolomics and Metabolic Profiling." Anal. Chem., 87, 2015, pp. 133-146.

Astle, W. et al., "A Bayesian Model of NMR Spectra for the Deconvolution and Quantification of Metabolites in Complex Biological Mixtures.", J. Am. Stat. Assoc., 107, 2012, pp. 1259-1271.

Gomez, J. et al., Dolphin: A tool for automatic targeted metabolite profiling using 1D and 2D 1H-NMR data. Anal. Bioanal. Chem. 406, 2014, pp. 7967-7976.

Hao, J. et al. "Bayesian deconvolution and quantification of metabolites in complex 1D NMR spectra using BATMAN", Nat. Protoc. 9, 2014, pp. 1416-1427.

Jiang, L. et al., Eliminating the dication-induced intersample chemical-shift variations for NMR-based biofluid metabonomic analysis. Analyst 137, 2012, pp. 4209-4219.

Emwas, A. -H. et al. "Standardizing the experimental conditions for using urine in NMR-based metabolomic studies with a particular focus on diagnostic studies: a review.", Metabolomics 11, 2014, pp. 872-894.

Wishart, D.S. et al., HMDB: The Human Metabolome Database. Nucleic Acids Res. 35, 2007, pp. D521-D526.

Bouatra, S. et al, "The human urine metabolome.", PLoS One 8, e73076, 2013.

Ravanbakhsh, S. et al., "Accurate, Fully-Automated NMR Spectral Profiling for Metabolomics", PLoS One 10, 2015 e0124219.

Xia, J. et al., MetaboMiner—Semi Automated identification of metabolites from 2D NMR spectra of complex biofluids. BMC Bioinformatics 9, 2008, pp. 1-16.

Zheng, C. et al., Identification and quantification of metabolites in 1H NMR spectra by Bayesian model selection, Bioninformatics 27, 2011, pp. 1637-1644.

Wishart, D. S. et al., HMDB: A Knowledgebase for the human metabolome, Nucleic Acids Res. 37, 2009, D603-10.

Athersuch, T. J. et al., Evaluation of 1H NMR Metabolic Profiling Using Biofluid Mixsture Design, Anal. Chem. 85, 2013, 6674-6681.

Sokolenko, S. et al. Profiling convoluted single-dimension proton NMR spectra: A plackett-burman approach for assessing qualification error of metabolites in complex mixtures with application to cell culture, Anal. Chem. 86, 2014, pp. 3330-3337.

Friedman, J.H., "Multivariate adaptive regression splines", Ann State 19, 1991, pp. 1-141.

Aranjbar, et al. "Metabolomie analysis using optimized NMR and statistical methode", Anal. Biochem., 2006, 355 (1), pp. 62-70.

Saude et al., "Optimization of NMR analysis of biological fluids for quantitative accurancy", Metabolomics 2 (2006).

Janich, M.A. et al., "Effects of pyruvate dose on in vivo metabolism and quantification of hyperpolarized 13C spectra", NMR in Biomedicine, vol. 25, No. 1 10 pages.

Jerk Ronnels et al., Complete 1H and 13C NMR chemical shift assignments of mono- to tetrasaccharides as basis for NMR chemical shift predictions of oligosaccharides using the computer program CASPER, Cabrohydrate Research, Jul. 10, 2013, vol. 380, p. 156-166.

* cited by examiner

METHOD FOR PREDICTING CHEMICAL SHIFT VALUES OF NMR SPIN SYSTEMS IN A SAMPLE OF A FLUID CLASS, IN PARTICULAR IN A SAMPLE OF A BIOFLUID

CROSS REFERENCE TO RELATED APPLICATIONS

This application claims foreign priority under 35 U.S.C. § 119(a)-(d) to European Application No. EP16174410.7 filed on Jun. 14, 2016, the entire contents of which are hereby incorporated into the present application by reference.

FIELD OF THE INVENTION

The invention relates to a method for predicting chemical shift values of nuclear magnetic resonance (NMR) spin systems belonging to compounds contained in a sample of a fluid class using NMR spectroscopy.

NMR spectroscopy is a powerful tool for investigating the qualitative and quantitative composition of samples. In modern biochemistry and medicine, the composition of biofluids such as urine is of high value for scientists and physicians. Similarly, in chemistry and food technology, for example, the composition of samples is of high importance, in particular for quality control.

BACKGROUND

In general, 1-dimensional NMR experiments are employed to study a sample of a biofluid. In an NMR spectrum recorded from the sample, NMR spin systems of compounds contained in the sample produce NMR signals (peaks). Through use of the shape and size of a peak or peaks belonging to the NMR spin systems of a particular compound, the concentration of this compound can be determined.

However, in a typical biofluid such as urine, numerous compounds which have relevant NMR spin systems are contained, and so their corresponding peaks overlap. The same applies in general to samples of other fluid classes. Further, peak positions of the same NMR spin systems may vary from sample to sample, depending on characteristics of the sample such as its pH, temperature, or concentration of substances (or metabolites) contained. This makes it difficult to attribute peaks found in the NMR spectrum to the correct NMR spin systems or compounds, respectively. Attributing a peak to an NMR spin system is therefore, as a rule, an experienced expert's job requiring plenty of time, and even an experienced expert may do a wrong assignment, leading to wrong qualitative or quantitative composition information.

In a procedure known as spiking, after having recorded an NMR spectrum of the sample, a compound of interest is enriched in a sample, and another NMR spectrum is recorded. By comparison of the NMR spectra of the original sample and the enriched sample, in particular the increase of particular peak intensities, a more reliable attribution of peaks may be achieved. However, this procedure is very elaborate, and changes the composition of the original sample.

There are also computer-assisted peak identification tools, however, these generally require high computational power or a long calculation time, and may not avoid occasional wrong peak allocations, leading to wrong "positive" results in chemical analysis. More specifically, BATMAN (the same stands for BQuant) uses the Monte Carlo Markov Chain algorithm to calculate a Bayesian model for each NMR spin system within a user's predefined ppm region, which requires considerable computational effort. Moreover, BATMAN (and BQuant) are not designed as fully automated assignment tools and they require each time, being built in databases for assigning and quantifying a metabolite. For BATMAN, running a small ppm range from one spectrum when fitting just two metabolites, takes on the order of half a minute, and for a typical data set of about 200 spectra, fitting about 25 metabolites may take several days with state of the art computer equipment.

In U.S. Pat. No. 7,191,069 B2 it is proposed to obtain an NMR test spectrum from a sample under a measured condition, such as a particular pH, and to use this measured condition for selecting a set of reference spectra of compounds suspected to be present in the sample from a library. By combing reference spectra from the set, a matching compound spectrum is produced, the peaks of which match the test spectrum's peaks. The compounds associated with the reference spectra used to produce the matching spectrum are considered indicative of the compounds contained in the sample.

US 2015/0099668 A1 discloses the use of 1H NMR spectroscopy for determining levels of biomarkers in a mammalian biological sample, and to compare these levels to one or more core biomarkers reference levels for characterizing metastatic disease.

SUMMARY

It is an object of the invention to allow a more reliable and easier, and in particular faster, attribution of peaks in an NMR spectrum of a sample of a fluid class, in particular, a biofluid, to NMR spins systems of compounds contained in the sample.

This object is achieved, in accordance with the invention, by a method for predicting chemical shift values of NMR spin systems belonging to compounds contained in a sample of a fluid class using NMR spectroscopy comprising:
a) providing a model appliance representing an information of correlation between captured characteristics of the fluid class, wherein the captured characteristics include concentrations of captured substances contained in the fluid class, and chemical shift values of captured NMR spin systems belonging to compounds contained in the fluid class, wherein the compounds are among the captured substances, wherein the model appliance comprises a definition of reference NMR spin systems, wherein the reference NMR spin systems are a subset of the captured NMR spin systems, wherein the reference NMR spin systems belong to compounds which are omnipresent in the fluid class,
b) recording an NMR spectrum of the sample of the fluid class;
c) identifying peaks in the recorded NMR spectrum which belong to the defined reference NMR spin systems of the model appliance, and determining experimental chemical shift values of the peaks from the recorded NMR spectrum;
d) predicting a chemical shift value of at least one of the captured NMR spin systems not belonging to the reference NMR spin systems by applying the model appliance onto the experimental chemical shift values of the reference NMR spin systems.

The present invention proposes to identify initially only a few peaks in a recorded NMR spectrum of a sample of a fluid class which belong to predefined reference NMR spin systems, and to determine their chemical shift values (or peak positions) from the recorded NMR spectrum. Through use of a model appliance, the chemical shift values of one or a multitude of other peaks belonging to NMR spin systems which are not reference NMR spin systems ("non reference NMR spin systems") are predicted, based on the experimental chemical shift values of the reference NMR spin systems. These predictions can be used for a highly reliable peak identification.

The invention exploits the fact that a particular characteristic of a sample, such as the concentration of a particular substance contained, influences the positions of peaks belonging to numerous NMR spins systems of different compounds at the same time. In turn, this is true for numerous characteristics of the sample, in particular the concentration of the substances contained, at the same time. This means that the positions of peaks belonging to the numerous NMR systems of different compounds contained are interdependent from each other via the numerous characteristics of the sample, in particular the concentrations of substances contained.

The inventors found that due to the interdependency of the peak positions of the numerous NMR spin systems, it is enough to know the peak positions of a subset (i.e. a part) of the NMR spin systems of interest, namely of the reference NMR spin systems, in order to predict the peak positions of other NMR spin systems, namely the non-reference spin systems, with a good accuracy. Through use of the predicted peak position (or chemical shift value) of a peak belonging to a particular NMR spin system of interest, it is easy to identify the corresponding peak in the recorded NMR spectrum. In general, the peak in the recorded NMR spectrum closest to the predicted peak position for an NMR spin system will be considered as the peak belonging to the respective NMR spin system. The invention reduces the need for conventional peak identification to a small number of reference peaks, and allows a simplified peak identification of the peaks of non-reference NMR spin systems.

The reference NMR spin systems are generally chosen such that their corresponding peaks may easily be identified in the spectrum, e.g. since their peaks are significantly more intense than all other peaks nearby, or they are easily distinguished from other peaks nearby based upon their characteristic shape-pattern, for all combinations of characteristics of the sample that can reasonably be expected for this fluid class (e.g. type of biofluid). The peaks belonging to the reference NMR spin systems can be identified in the recorded NMR spectrum of the sample manually (even by non-experts) or automatically by a suitable software, typically exploiting a known chemical shift interval in which the peak will show up and/or applying checking criteria such as same peak integrals or intensities for doublets etc. Further, the compound belonging to a reference NMR spin system should be present in any sample of the fluid class in a minimum concentration, relevant for influencing other NMR spin systems ("omnipresent compound"). Further, the compound belonging to a reference NMR spin system should significantly influence a considerable number of NMR spin systems (possibly including itself).

The intercorrelation information for the fluid class to which the sample belongs is stored in a model appliance, which is preferably based on information from a teaching database. The teaching database comprises for a large amount of test samples the sample characteristics, in particular substance concentrations, and chemical shift values (peak positions) belonging to NMR spin systems of compounds contained, as identified in an NMR spectrum. The model appliance may be derived in advance, so when later calculating predicted chemical shift values in step d), the final model appliance only needs to be applied, what can be done rather fast (as a matter of seconds), generally only requiring the solving of a few equations. The model appliance is typically implemented as a software tool, preferably operating fully automatically.

It should be noted that the model appliance (and the underlying teaching database) correlates a finite number of NMR spin systems (or their respective chemical shift values) and a finite number of characteristics. In general, the more characteristics are included in the model appliance, the more accurate the prediction of chemical shift values can be. In general, it is desirable to include at least the concentrations of the most abundant substances in the fluid class into the model. Further, the more NMR spin systems that are covered, the more peaks in an NMR spectrum that may be predicted.

Further, the more reference NMR spin systems that are used, the more accurate will be the predictions of the chemical shift values of the non-reference NMR spin systems. However, when using too many reference NMR spin systems, the peak identification of step c) will in general become more difficult and time consuming. Therefore, for the number R of reference peak systems, it is preferred that $3 \le R \le 8$. In relation to the number of N non-reference NMR spin systems captured, it is preferred that $R \le \frac{1}{4} *N$.

A fluid class is characterized by a number of substances which are contained in any sample of the fluid class, albeit in varying concentrations (omnipresent substances), and often also by a number of substances which are sometimes contained in samples of the fluid class, in varying concentrations (occasional substances). In general, the substances occur in limited ranges of concentrations, or limited ranges of concentration ratios in the samples of the fluid class. Typically, there are at least ten omnipresent substances that can be found (or defined) for a fluid class, and sometimes even 50 or more omnipresent substances can be found (or defined) for a fluid class. In accordance with the invention, the fluid class is in general of aqueous type, with a water content of at least 10 weight %.

A typical fluid class is a particular biofluid (such as urine or blood serum) of a particular species (such as humans or cats); sample variations typically occur from person to person, or due to illness, for example. In biofluids, the substances are generally metabolites. Other fluid classes may be bodycare lotions, condiments (such as ketchup) or energy drinks, for example.

A substance captured by the model appliance for a particular fluid class may be an omnipresent substance or an occasional substance known for the fluid class. In general, the model appliance captures only a part of the known omnipresent and/or occasional substances for the fluid class.

Compounds are omnipresent substances and/or occasional substances having one or more NMR spin systems. Compounds belonging to reference NMR spin systems are chosen from the (captured) omnipresent substances having one or more NMR spin systems.

The NMR spin systems are typically 1H NMR spin systems. The NMR spectrum is typically a 1-dimensional NMR spectrum.

In the previous and in the following, the term "captured" means that the referred parameter is contained in the correlation information of the model appliance or the teaching database, respectively. "Characteristics" of a sample may comprise substance concentrations, pH value and/or temperature T. As used herein, "substance" means molecules and/or ions (including inorganic ions) in the fluid class; note that a single type of ion (such as Cl⁻) without a counter ion may qualify as a substance here. As used herein, "metabolites" mean substances, i.e. molecules and/or ions (including inorganic ions) in a biofluid. As used herein, "compound" means a substance with at least one NMR spin system. The captured NMR spin systems comprise the reference NMR spin systems and the non-reference NMR spin systems.

Variants Referring to the Reference NMR Spin Systems

In a preferred variant of the inventive method, the reference NMR spin systems are chosen from those captured NMR spin systems, the chemical shift values of which are of significance for an above average amount of concentrations of captured substances, as determined by the model appliance. This reduces prediction errors. Preferably, the reference NMR spin systems are chosen such that they have the highest amounts of significantly influenced concentrations. Generally, the reference NMR spin systems should come with strong peaks far away from other peaks, so they can safely be identified in the recorded NMR spectrum for different sample compositions, either manually or automatically. The amount of significantly influenced concentrations can e.g., be determined through use of Analysis of Variance (ANOVA) decomposition applied to the items $j=1, \ldots, C$ of the second sub-model of full type (see below). Further, the reference NMR spin systems are preferably chosen such that each substance concentration significantly influences at least two chemical shift values of reference NMR spin systems.

In another preferred variant, the reference NMR spin systems are determined using a statistical correlation analysis method, in particular an ANOVA decomposition or Spearman's rank correlation or Kendall's Rank correlation or spurious calculation or canonical correlation analysis. The statistical correlation analysis method distinguishes chemical shift values of NMR spin systems of high relevance for substance concentrations (or more generally sample characteristics) from those of low relevance, so NMR spin systems coming with a high relevance (preferably the highest relevance) may be chosen as NMR reference peaks. The statistical correlation analysis methods can be used for example to identify the amount of significantly influenced concentrations through a particular chemical shift value of an NMR spin system. Note that the abundance of an NMR spin system or its composite, respectively, may also be taken into account when choosing the reference NMR spin systems.

Variants Referring to Sub-models

In a preferred variant, the model appliance comprises a first sub-model of reduced type which indicates the captured characteristics $x_j$ as a function f of the chemical shift values $\delta_i$ of the reference NMR spin systems only, with $$x_j = f_j(\delta_1, \ldots, \delta_R),$$

with j: index of captured characteristics, with $j=1, C$ and C: number of captured characteristics, and with i: index of reference NMR spin systems, with $i=1, \ldots, R$ and R: number of reference NMR spin systems. Preferably, $3 \leq R \leq 8$. This first sub-model of reduced type gives a basis for applying the first sub-model of full type (see below) in order to identify the chemical shift values of the non-reference NMR spin systems. The first sub-model of reduced type can also be used for a coarse estimate of the characteristics of the sample.

Also preferred is a variant wherein the model appliance comprises a second sub-model of reduced type which indicates the chemical shift values $\delta_k$ of the non-reference NMR spin systems as a function f of the chemical shift values $\delta_i$ of the reference NMR spin systems only, with $$\delta_k = f_k(\delta_1, \ldots, \delta_R),$$

with k: index of non-reference NMR spin systems, with $k=1, \ldots, N$ and N: number of captured non-reference NMR spin systems, and with i: index of reference NMR spin systems, with $i=1, \ldots, R$ and R: number of reference NMR spin systems. The second sub-model of reduced type can directly give a coarse estimate of the chemical shift values of the non-reference NMR spin systems. However, the second sub-model of reduced type can also give a basis for applying the second sub-model of full type and the first sub-model of full type (see below) to obtain an improved estimate of the chemical shift values of the non-reference NMR spin systems. Note that the model appliance may comprise only one of the first and second sub-models of reduced type, or both.

In another preferred variant, the model appliance comprises a first sub-model of full type which indicates the chemical shift values $\delta_l$ of the non-reference NMR spin systems or all captured NMR spin systems, as a function f of the captured characteristics $x_j$, with $$\delta_l = f_l(x_1, \ldots, x_C),$$

with l: index of NMR spin systems, with $l=1, \ldots, N$ and N: number of non-reference NMR spin systems or with $l=1, \ldots, S$ and S: number of all captured NMR spin systems, and with j: index of captured characteristics, with $j=1, \ldots, C$ and C: number of captured characteristics. The first sub-model of full type allows prediction of the chemical shift values at least of the non-reference NMR peaks, so together with the experimental chemical shift values of the reference NMR spin system, a full set of chemical shift values of all covered NMR spin systems may be obtained, based on the full set of covered characteristics. This can be used in an iterative process for improved prediction accuracy. If the first sub-model of full type also predicts chemical shift values of some or all reference NMR spin systems, a comparison of the experimental and predicted chemical shift values allows an estimate about the degree of convergence reached in multiple applications of the model appliance (see below).

Further preferred is a variant wherein the model appliance comprises a second sub-model of full type which indicates the characteristics $x_j$ as a function f of the chemical shift values $\delta_l$ of the captured NMR spin systems, with $$x_j = f_j(\delta_1, \ldots \delta_S),$$

with j: index of captured characteristics, with $j=1, \ldots, C$ and C: number of captured characteristics, and with l: index of captured NMR spin systems, with $l=1, \ldots, S$ and S: number of captured NMR spin systems. The second sub-model of full type allows to prediction of the full set of captured characteristics based on the full set of chemical shift values (which are typically partially experimental and partially predicted, but may also be all experimental or all predicted). The second sub-model of full type is usually part of an iterative process for obtaining the predictions of the chemical shift values of the non-reference NMR spin systems; it can also be used to obtain an estimate of characteristics, in particular substance concentrations, including concentrations of substances that are not NMR active such as ions.

In a further development applying the variants introducing the first sub-model of reduced type and the two sub-models of full type as described above, during step d), the following substeps are applied:

d1) the first sub-model of reduced type is applied onto the experimental chemical shift values of the reference NMR spin systems to obtain predicted characteristics;
d2) the first sub-model of full type is applied onto the predicted characteristics of previous substep d1) to obtain predicted chemical shift values of the non-reference NMR spin systems;
d3) the second sub-model of full type is applied onto the experimental chemical shift values of the reference NMR spin systems and the predicted chemical shift values of the non-reference NMR spin systems obtained in previous substep d2) to obtain predicted characteristics;
d4) the first sub-model of full type is applied onto the predicted characteristics obtained in previous substep d3) to obtain predicted chemical shift values of the non-reference NMR spin systems;
in particular wherein the sequence of substeps d3) and d4) is repeated several times, starting with the predicted chemical shift values of the non-reference NMR spin systems obtained in the previous step d4). This allows a relatively accurate prediction of chemical shift values of the non-reference spin systems. By applying the sequence of steps d3) and d4) several times, a convergence of the chemical shift values occurs, improving the prediction quality.

In another further development applying the variants introducing the second sub-model of reduced type and the two sub-models of full type as described above, during step d), the following substeps are applied:
d1') the second sub-model of reduced type is applied onto the experimental chemical shift values of the reference NMR spin systems to obtain predicted chemical shift values of the non-reference NMR spin systems;
d2') the second sub-model of full type is applied onto the experimental chemical shift values of the reference NMR spin systems and the predicted chemical shift values of the non-reference NMR spin systems obtained in previous substep d1') to obtain predicted characteristics;
d3') the first sub-model of full type is applied onto the predicted characteristics obtained in previous substep d2') to obtain predicted chemical shift values of the non-reference NMR spin systems;
in particular wherein the sequence of steps d2') and d3') is repeated several times, starting from the predicted chemical shift values of the non-reference NMR spin systems obtained in the previous step d3'). This again allows a relatively accurate prediction of chemical shift values of the non-reference spin system. By applying the sequence of steps d2') and d3') several times, a convergence of the chemical shift values occurs, improving the prediction quality.

Variants Referring to the Teaching Database

Particularly preferred is a variant wherein the model appliance is derived from a teaching database, the teaching database comprising for each of a plurality of teaching samples of the fluid class
  values of the captured characteristics, including values for the concentrations of the captured substances,
  and chemical shift values of the captured NMR spin systems, obtained through use of a teaching NMR spectrum recorded of the respective teaching sample and assignment, in particular manual assignment, of peaks in the teaching NMR spectrum to the captured NMR spin systems and determining their chemical shift values. The teaching database can provide the correlation information required for the model appliance. Note that in principle, quantum mechanical calculations may also be applied to obtain the correlation information, but this is relatively difficult to do. A typical number of characteristics is 20 or more, typically with at least ten characteristics being concentrations of compounds belonging to captured NMR spin systems, and at least five characteristics being concentrations of NMR inactive substances (e.g., ions such as chloride ions or oxonium ions). Another characteristic may be the sample temperature or pH (if the latter is not treated as a concentration of a substance). A typical number of NMR spin systems captured (covered) is at least 20. The total number of teaching samples contained in the database is typically at least 500, preferably at least 1000, and particularly preferred at least 3000. The teaching samples (and the measured sample) belong to a particular fluid class. The fluid class may in particular be chosen to correspond to a particular type of biofluid such as urine. The teaching samples represent different compositions of this fluid class, preferably in a range expected to occur in the measured sample, e.g., in biofluids due to different illnesses or simply due to different persons or origin (but typically not due to different species such as human and dog). The same applies to plant derived products, it should be the same product, e.g., apple juice, from various origins. It should be noted that once a model appliance has been completely derived from the teaching database, the teaching database is no longer needed to apply the inventive method.

In a further development of this variant, at least a part of the teaching samples of the fluid class are artificial samples of the fluid class, in particular wherein the artificial teaching samples only contain substances captured by the model appliance. For artificial samples, the concentrations may be set and are therefore well known. Further, when containing only a limited number of substances (such as the captured substances), peak identification for the purpose of preparing the teaching database is easier. This further development is particularly useful when the fluid class corresponds to a biofluid, where "natural" samples are difficult to obtain, and peaks in "natural" samples are hard to identify when establishing the teaching database since a very large amount of compounds may be contained.

In another advantageous further development, for each captured substance, teaching samples of at least three, preferably at least five, different concentrations are comprised. This keeps prediction errors low. Preferably, the different concentrations comprised for a captured substance cover the range in which the concentration of the substance in the sample is; else the prediction has a larger error. For biofluids, a typical covered range is determined by maximum and minimum concentrations of a metabolite naturally occurring in the biofluid chosen, which often can be found in the literature. For artificial products, industrial norms may imply a covered range.

A preferred further development provides that the captured characteristics include a temperature, and that for each set of concentrations of metabolites, teaching samples of at least two different temperatures are comprised. When including temperature in the captured characteristics, sample NMR spectra acquired at different temperatures can be handled by the invention with increased prediction accuracy. Further, it is noted that a particular tempering of the sample during recording of the NMR spectrum becomes unnecessary.

In an advantageous further development, the model appliance, or one or a plurality of its sub-models, is derived from the teaching database through use of a multivariate statistical algorithm, in particular wherein the multivariate statistical algorithm is a self-learning algorithm. Multivariate statistical algorithms provide a powerful tool for extracting the correlation information from the teaching database and putting it into the model appliance or its sub-models, respectively. In this context, self-learning means that additional teaching samples (or their chemical shift values and characteristics, respectively) can be integrated into the teaching database such that statistical output of the correlation, i.e. the model appliance, can be continuously improved, and/or that the method can be extended to further compounds (or additional NMR spin systems of compounds and their concentrations, respectively) which are present in the fluid class.

For the above further development, the multivariate statistical algorithm may be selected from Multivariate adaptive regression (linear and cubic) splines (MARS) models, (Orthogonal) Partial Least Squares (PLS) discriminant analysis, Principal Component Analysis, Principal Component regression, Multiple linear regression, Locally weighted regression, Mahalanobis distance based analysis, Soft Independent Modelling of Class Analogy (SIMCA), K-nearest neighbour method, Support Vector Machine (SVM) Analysis, Linear discriminant analysis or Classical Least Square discriminant analysis, Artificial Neural Networks, Hierarchical modelling/clustering, Distribution-based clustering, or Parallel factor analysis.

Other Vriants

A preferred variant provides that the fluid class is chosen as a biofluid, in particular wherein the captured substances are metabolites. Biofluids contain particularly large numbers of compounds, which makes (conventional) peak identification very difficult, so the inventive method is particularly useful here. For biofluids, omnipresent substances and occasional substances as well as their concentration ranges or concentration ratio ranges can often be found in literature, so a teaching database can easily be drafted. It should be noted that samples of biofluids can be handled in an undiluted state or in a diluted state, if necessary or desired, in accordance with this variant.

In a preferred further development of this variant, the biofluid is a body fluid, preferably selected from urine, blood serum, sweat, saliva or CSF (cerebrospinal fluid), or that the biofluid is a plant fluid, preferably selected from fruit juice, chyle or nectar. With body fluids, after the inventive analysis, the NMR spectra can be used for a highly reliable identification of illnesses. As far as plant fluids are concerned, the NMR spectra can be used for a more accurate quality control or verification of origin.

In another preferred variant, the fluid class is chosen as a naturally derived product, in particular plant derived product, preferably selected from wine, honey or condiments. Again, after the inventive analysis, the NMR spectra can be used for a more accurate quality control or verification of origin.

In an advantageous variant, the fluid class is buffered to a pH range between 6.6 and 7.5, in particular using a phosphate buffer. This procedure limits the chemical shift value variations, thus simplifying the prediction of the chemical shift values. Note that some types of fluid classes, in particular some types of biofluid such as blood serum, are inherently buffered, so no additional buffering is needed in the sample/test samples.

Methods Referring to Concentration Determination

Also within the scope of the present invention is a method for determining a concentration of at least one substance contained in a sample of a fluid class by NMR spectroscopy, with the following steps:

aa) predicting the chemical shift values of non-reference NMR spin systems of the captured NMR spin systems according to steps a) through d) of the inventive method described above, bb) identifying peaks in the recorded NMR spectrum which belong to non-reference NMR spin systems through use of the predicted chemical shift values, and determining experimental chemical shift values of the peaks from the recorded NMR spectrum;

cc) calculating the concentration of the at least one substance by applying the model appliance onto the experimental chemical shift values of the reference NMR spin systems and non-reference NMR spin systems, in particular by applying the second sub-model of full type described above. This method can provide a good prediction of substance concentrations, without any complex peak integration or lineshape fitting. It is relatively accurate, since it uses experimental chemical shift values for both reference and non-reference NMR spin systems. Preferably, all captured NMR spin systems are used in step cc). Note that in step bb), if a peak cannot be found in the recorded NMR spectrum because it is too weak, the predicted chemical shift value can be taken as an experimental chemical shift value for the purpose of next step cc).

Further within the scope of the present invention is a method for determining a concentration of at least one substance contained in a sample of a fluid class by NMR spectroscopy, with the following steps:

aa') predicting the chemical shift values of non-reference NMR spin systems of the captured NMR spin systems according to steps a) through d) of the inventive method described above, bb') calculating the concentration of the at least one substance by applying the model appliance onto the experimental chemical shift values of the reference NMR spin systems and the predicted chemical shift values of the non-reference NMR spin systems obtained in step aa'), in particular by applying the second sub-model of full type described above. This method can provide a fast prediction of substance concentrations, without any complex peak integration or lineshape fitting. Since only the peaks of the reference NMR spins systems have to be identified in the NMR spectrum, it can be done in a short time. Preferably, all captured NMR spin systems are used in step bb').

In a preferred variant of the above two methods, the at least one substance the concentration of which is determined by NMR spectroscopy comprises an NMR inactive substance, in particular, an ion. An NMR inactive substance (i.e. a substance not having an NMR spin system, so no peak belongs to this substance in the recorded NMR spectrum) can be analysed for concentration, via its impact to the position of peaks of NMR spin systems in other substances, through use of the invention. Note that NMR inactive substances such as $Cl^-$ ions are not accessible via conventional NMR based concentration determination, since they have no peak in the NMR spectrum that might be integrated or used for lineshape fitting.

Within the scope of the present invention is further a method for determining the concentration of at least one compound contained in a sample of a fluid class, with the following steps:

aa") predicting the chemical shift value of at least one NMR spin system belonging to the compound according to steps a) through d) of an inventive method as described above, wherein the at least one NMR spin system is a non-reference NMR spin system, bb") identifying at least one peak in the recorded NMR spectrum of the sample which belongs to the at least one NMR spin system through use of the predicted chemical shift value, cc") calculating the concentration of the compound based on the shape and/or size of the identified at least one peak in the recorded NMR spectrum of the sample, in particular through use of peak integration and/or lineshape fitting. In this method, the correlation information of the model appliance is used for a fast and reliable identification of at least one peak in the recorded NMR spectrum, and then conventional concentration determination is applied, e.g., using peak integration or lineshape fitting. This results in particularly accurate and reliable concentration information on compounds. Note that step cc") is typically done with a separate software module.

Further advantages can be extracted from the description and the enclosed drawing. The features mentioned above and below can be used in accordance with the invention either individually or collectively in any combination. The embodiments mentioned are not to be understood as exhaustive enumeration but rather have exemplary character for the description of the invention.

BRIEF DESCRIPTION OF THE DRAWINGS

The invention is shown in the drawing.

FIG. 6 17 metabolites concentrations and pH values distributions in 20 randomly prepared artificial urine mixtures (top figure) and their corresponding predictions errors distribution in the presented embodiment of the inventive method.

FIG. 8 7 metabolites concentrations distributions in 20 randomly prepared artificial urine mixtures (top figure) and their corresponding predictions errors distribution in the presented embodiment of the inventive method.

FIG. 12 The 7 metabolites' 10 $^1$H spin systems NMR chemical shifts (indicated by the arrows) that appear as significant variables for concentrations, pH and T models. The dashed circles highlight the most easily assigned in urine biofluid NMR profiles.

DETAILED DESCRIPTION

Figure 1:
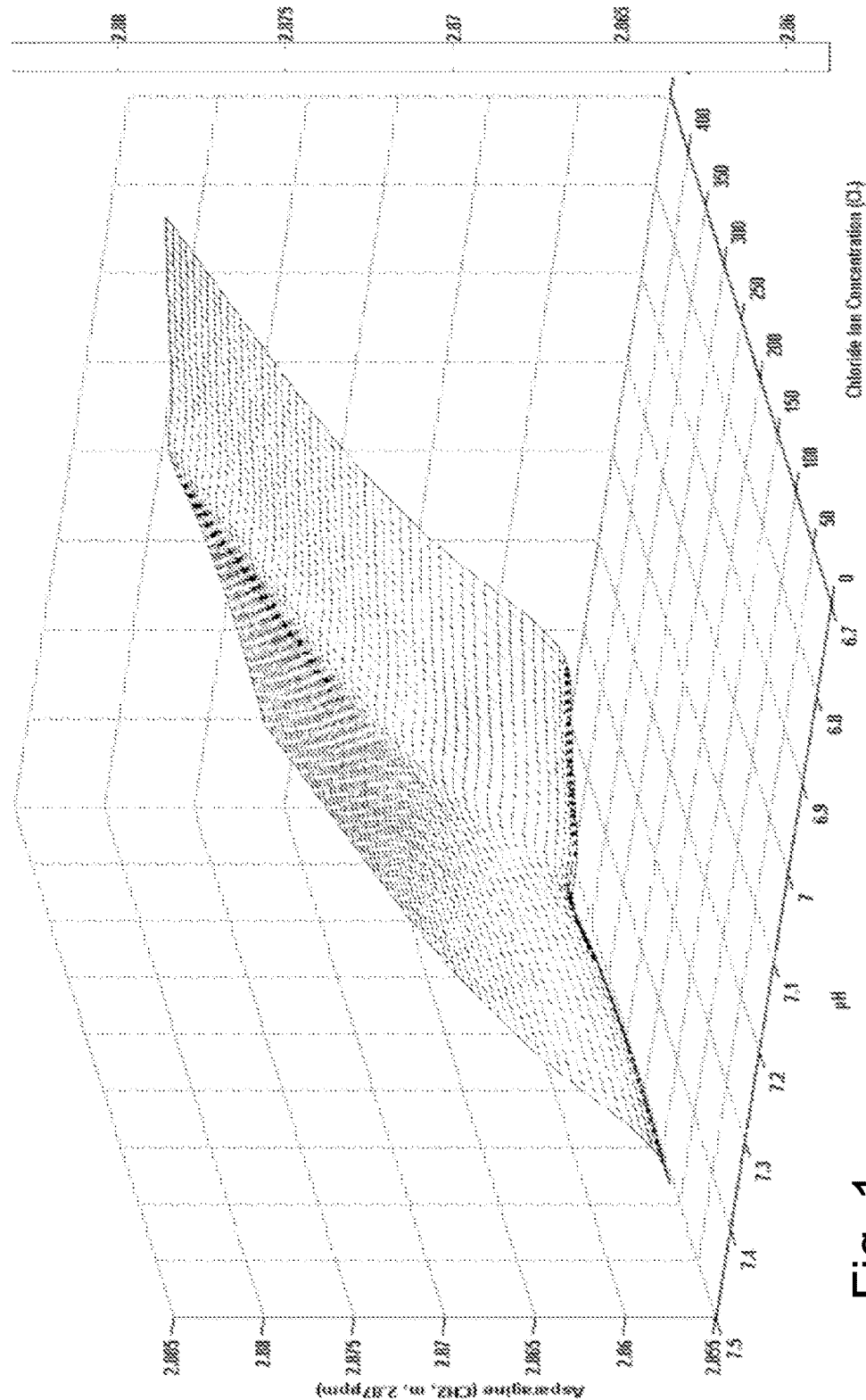
FIG. 1 L-Asparagine's spin system —$CH_2$ multiplet $\delta_O$ chemical shift values interpolation by its fitted model as pH and chloride ions concentration (mM) change in artificial urine mixtures.

In the following, the inventive method is explained in more detail by way of an embodiment wherein a particular biofluid, namely human urine, has been chosen as the fluid class to which the model appliance and test samples, as well as the samples to be investigated relate. Accordingly, in this embodiment, the captured substances of the model appliances are metabolites. However, it should be stressed that the invention is also applicable to other fluid classes, in particular other types of biofluid such as blood serum, or types of artificial products such as shower gels, or types of nature or plant derived artificial products such as ketchup, for example.

The growth of metabolomics and other "omics" fields indicates their significance in modern system biology studies, due to their ability to extract detailed information of the organisms' metabolome, proteome and genome.[1,2] In the framework of metabolomics, various spectroscopic, spectrometric or biochemical techniques are employed. Among them is NMR spectroscopy—in general through 1D-NMR experiments—because of its rapid, accurate and nondestructive features.[3]

Metabolomics studies require the identification of metabolites in complex mixtures such as biofluids.[4-6] The difficulty arises from the large number of metabolites. In the NMR spectra of biofluids, many metabolites' signals are overlapped due to magnetically equivalent $^1$H nuclei and/or some of them are hidden by the peaks of more abundant metabolites of the biofluid's matrix. However, the biggest challenge arises from NMR chemical shifts variations due to pH, ionic strength as well as chemical-electrostatic interactions among metabolites.[7] This problem is particularly serious for the biofluids that exhibit a high variety of metabolites' content, ionic strength and pH variability, such as urine. Urine composition is not regulated by homeostasis rules as are plasma/serum and CSF biofluids; yet, it is probably the most valuable biofluid for metabolomics, due to its collection—sample preparation simplicity, abundance and rich content of metabolic information.[8] So far, more than 3000 substances (organic, inorganic, ionic substances, as well as proteins in small amounts),[9] are detected in human urine and, among them, around 300 metabolites have been detected-quantified by means of NMR spectroscopy.[10]

To assign and quantify metabolites the following approaches are commonly employed:

i) manual assignment-quantification. This approach consists of compounds spiking in the biofluid sample and peak integration, use of software such as Chenomx NMR Suite, exhaustive inquiry in metabolites NMR spectra databases and/or spectra binning. Spiking many metabolites is costly and time consuming, and could significantly alter the composition of the biofluid matrix, thus contributing to peaks shifting due to previously non-existing interactions, and the other manual assignment procedures require extensive NMR experience on working with biofluids.

ii) use of semi-automated computational tools. Bayesil,[11] MetaboMiner,[12] etc. are some of the most known software tools, which provide several metabolites (around 50 for serum/plasma samples by Bayesil) quantification from a $^1$H-NMR spectrum, while allowing the user to improve the assignment-fitting of the metabolites' $^1$H-NMR peaks. However, the use of a specific protocol is required for the sample preparation and NMR acquisition, and experience in NMR analysis of biofluids is still a prerequisite for the accurate metabolites assignment.

iii) use of automated computational approaches like the BATMAN algorithm,[6] Dolphin[5] and BQuant.[13] BATMAN (the same applies for BQuant) is an almost automated tool. In general, it uses a MCMC estimation of the Bayesian model for the best fitting of a metabolite's $^1$H spin system, with a view to its quantification. A significant amount of computational power, prior knowledge of metabolites' NMR peaks position range, as well as prior database construction are usually required to get as many true positive results as possible. Yet, several false positive results are obtained due to wrong NMR peak assignments. The Dolphin software package appears computationally "lighter" than BATMAN, it is still based upon databases information (i.e. HMDB, BMRB, etc.), while taking advantage of the 2D-JRES spectra increases the accuracy of the metabolites' assignment and consequently their quantification. Apart from the need of high resolution 2D-JRES spectra, the user should define a list of metabolites to quantify. However, not all metabolites contain coupled $^1$H nuclei and many of them exhibit only singlet(s), and often their NMR signals resonate in the same spectral region, again leading to false positive assignments.

In conclusion, the key prerequisite for a successful and accurate metabolites' concentration determination is the flawless assignment of their signals. The previous approaches require computational time or computational power or extra NMR experiments or user's high NMR experience, and still do not guarantee 100% metabolites' assignment (therefore quantification) success.

The present invention presents a new approach for assigning compounds, here metabolites, or their NMR spin systems, respectively, to their peaks in an NMR spectrum. The inventive method, or its model appliance, respectively, can be implemented in a fully automated computational tool.

The model appliance has already built in position models for each of a number of NMR spin systems, made previously through use of mixtures (test samples), and each time works totally automated (blind). It does not use any fitting procedures for the quantification and/or assignment of NMR signals. However, quantification may be done by integration or lineshape fitting by a downstream software, if desired. In practice, the model appliance simply solves an "equation" depending on sensor (reference) NMR signals ppm values and provides the output of compounds (here metabolites) NMR peaks positions as well as an estimation of their concentrations.

In the embodiment presented, the model appliance or the computational tool, respectively, automatically assigns 41 $^1$H NMR spin systems of 21 metabolites/compounds in a urine NMR sample, while providing an estimation of 5 further (molecular) metabolites/substances and 10 major ions concentrations with small relative error (<10%), of sample's pH value with <±0.1 error, as well as its temperature (T) during the NMR acquisition with ±0.1 K. An NMR spectrum may be analysed by the model appliance on the order of 10 seconds for providing a full set of predicted chemical shift values and sample characteristics, in particular, compound concentrations.

From the basics of NMR, it is known that the observed chemical shift ($\delta_O$) value of a spin system (here of $^1$H nuclei) of a compound in a solution mixture is the precise picture of the chemical environment around the nucleus, and it is highly affected by all kinds of molecular interactions that the compound experiences inside the solution mixture. However, the details of the effects of these multiple weak interactions on the chemical shifts are not predictable a priori. In general, under fast exchange conditions, the $\delta_O$ value can be related to the mole fraction of the corresponding compound molecules in the mixture, existing in numerous equilibrium states, namely those molecules that form any possible (self-) interaction with any context (n number of metabolites) of urine matrix ($X'_C$), and those that do not participate in the interaction ($X_f$):

$$\delta_O = X_f \delta_f + \sum_{n=1}^{i} X_C^n \delta_C^n, \qquad (1)$$

where $\delta_f$ and $\delta_C^n$ are the chemical shift values of the spin system of a metabolite in its interactions within itself and with n other metabolites (including all existing compounds in (here) the urine matrix), respectively. From eq. (1), it is clearly indicated that the $\delta_O$ values are directly correlated to the concentration of the interacting compounds. As previously mentioned, pH and T changes cause chemical shifts variations; consequently, each $^1$H-NMR $\delta_O$ value from any wine compound that contains $^1$H nuclei could be described by the following function:

$$\delta_O = f(x_1, \ldots, x_n), \qquad (2)$$

where variables x are the concentrations of each possible interacting compound, the pH and the T (also referred to as the sample's characteristics), whose contributions to each $^1$H nuclei NMR chemical shift rebound to its $\delta_O$ value.

In order to construct eq. 2, the mapping of all above mentioned contributions to each $\delta_O$ is needed. To achieve this, simulation of the real urine's content matrix states is obtained by constructing numerous mixtures of urine metabolites in various concentrations, acquiring their 1D $^1$H-NMR spectra and recording each $^1$H-NMR $\delta_O$ from each metabolite $^1$H spin system. For improving the simulation of urine, criteria have been applied for the selection of metabolites for the artificial urine samples construction. To do this, the most abundant 26 urine metabolites (of molecular type) as well as 10 ions (or metabolites of ion type) were selected according to HMDB (human metabolomics database) and other bibliographic reported concentrations and occurrence in urine biofluid (see, Example). Namely, the applied criteria were based upon 100% occurrence and high abundance of the molecular metabolites and ions as measured by NMR, MS, LC and other techniques in thousands of urine samples of healthy individuals.[14] Accordingly, the mixtures were prepared by changing in each mixture the concentration of one metabolite, using as starting point its lowest reported concentration until the mean one here (note that alternatively, also an interval from the lowest abnormal value to the highest abnormal value may be used), with typically 4 intermediate values. The same experimental scheme was followed for the pH adjustment of each mixture after the addition of the common urine buffer for $^1$H-NMR based metabolomics (see, Example). In Table 1, the designed structure of the mixtures is presented. In total 1235 mixtures were created.

TABLE 1

|  | Alanine (mM) | Serine (mM) | Na$^+$ (mM) | ... | n$^{th}$ compound | pH (5 values) |
|---|---|---|---|---|---|---|
| Mixture 1 | 0.0050 | 0.0035 | 1.0000 | ... | 0.0070 | 6.80-7.20 |
| Mixture 2 | 0.0100 | 0.0025 | 1.0000 |  | 0.0070 | 6.80-7.20 |
| Mixture 3 | 0.0050 | 0.0025 | 1.5000 |  | 0.0070 | 6.80-7.20 |
| . | 0.0050 | 0.0025 | 1.0000 |  | 0.0070 | 6.80-7.20 |
| Mixture n$^{th}$ | 0.0050 | 0.0025 | 1.0000 |  | 0.0040 | 6.80-7.20 |

Based upon Table 1, an artificial urine matrix was composed, where each row of the matrix contains the metabolites (molecular and ions) concentrations information, pH and the T of each artificial urine mixture, namely the x variables of eq. 2. The mixtures matrix (or first part of a teaching database) of the presented embodiment had the size of 1235×38, where 38 is the total number of variables (26 molecular metabolites/substances and 10 ion metabolites/substances concentrations plus pH and T values, i.e. the total number of captured characteristics C is 38). The 1H-NMR acquisition of each mixture (or test sample) produced one—reasonably simpler—spectrum compared to that of real urine, from which 41 $^1$H spin systems $\delta_O$ from 21 metabolites (compounds)—out of 26 metabolites—were manually assigned, i.e. the total number of captures spin systems S is 41. Based on their recorded chemical shift values (to the 4$^{th}$ decimal of ppm), a novel 1235×41 matrix (or second part of a teaching database) was composed, where each column contains the $\delta_O$ values of each spin system for 1235 artificial urine cases.

To the inventors' knowledge there has been neither such a systematic study for real biofluids simulation nor this kind of matrices (databases) construction based upon the NMR of simulated biofluids. Athersuch et al.[15] proposed that mixing different biofluid samples in known proportions according to a mixture design could improve some metabolites with overlapping NMR signals quantification. Sokolenko et al.[16] using the Plackett-Burman experimental design approach created some synthetic mixtures of 20 metabolites in order to deconvolute overlapped $^1$H-NMR resonances. In no case, was it considered that chemical shift changes due to changes in metabolite composition could be predicted.

As mentioned above, in general 6 different concentrations (from the low to the mean range in the presented embodiment) of each substance (molecular or ion metabolite), 5 pH values (6.8-7.2 range after buffer addition) and 2 temperature values (300.0 and 302.7 K) were used for the artificial urine content matrix. In order to derive the best correlation function (eq. 2) between each studied spin system $\delta_O$ values and all 38 variables (concentrations, pH, T), a multivariate statistical machine learning approach was employed, providing the best fitting as well as interpolation of the data. Multivariate adaptive regression (linear and cubic) splines models[17] (MARS models) (a number of similar machine learning multivariate approaches were tested, including artificial neural networks) exhibited the best cross-validated $R^2$ values and the lowest root mean square errors (RMSE) as well as the best predictability tested by various test datasets (see Example). In summary, the eq. 2 for each studied $^1$H spin system took the form of:

$$\delta_O = c_0 + \sum_{m=1}^{M} c_m B_m(x), \quad (3)$$

where, $c_0$ is the calculated constant value of the derived regression model, M is the number of linear or cubic spline basis function that are exploited for the best fitting model production, $c_m$ is the coefficient of the m$^{th}$ linear or cubic spline basis function, and $B_m(x)$ is the linear or cubic spline basis function. The calculated cross validated $R^2$ and RMSE values for the 41 (partial) model spin systems studied were >0.98 and <1e-04, respectively. In FIG. 1, the interpolation of the $\delta_O$ values of the L-Asparagine spin system —CH$_2$ multiplet (1 out of the 2) is depicted as a function of pH and chloride ions concentration.

Figure 2:
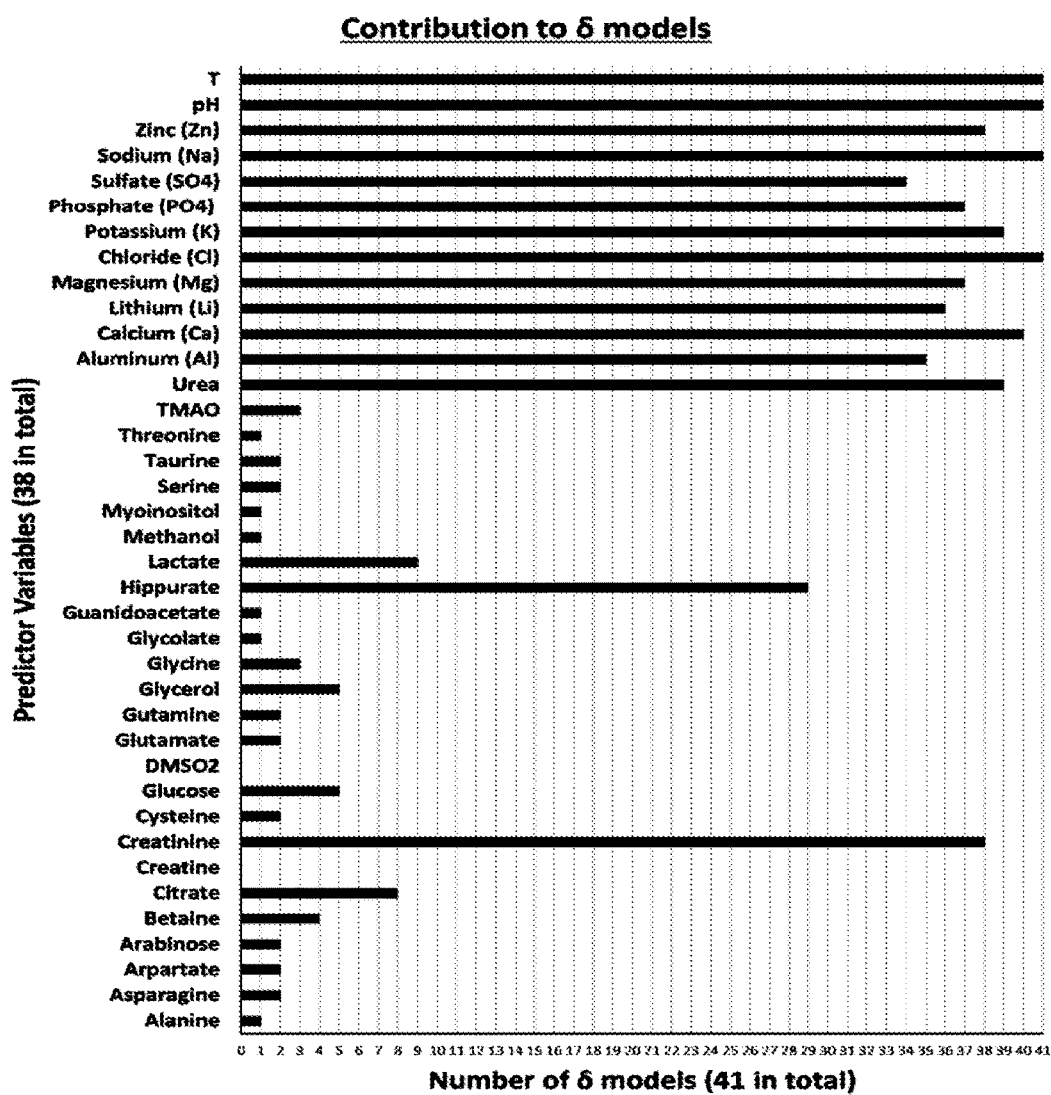
FIG. 2 Variables/characteristics (metabolite concentrations, pH, T) contribution to 41 $^1$H-NMR (partial) models. Bars indicate in how many models each variable is weighted (significant) for the fitting.

By performing an ANOVA decomposition of each (partial) model it was possible to detect all weighted variables, namely the variables that were significant for the construction of each model. As depicted in FIG. 2, the concentration of all ions (ion metabolites), of specific metabolites (such as urea, hippurate and creatinine), pH and T appear in almost all 41 models as significant variables. Bibliographic data[7] as well as primary chemical knowledge confirm the previous results, especially for the pH, T and ions impact on chemical shifts variations. In addition, the high concentration that creatinine, hippurate and urea usually exhibit in urine biofluid (as in the mixtures used here),[9] compared to all other metabolites, is the likely origin of the importance of these metabolites in determining the chemical shifts of many others, and in turn this finding corroborates the choice of selecting the most abundant metabolites in the initial metabolite panel.

Figure 3:
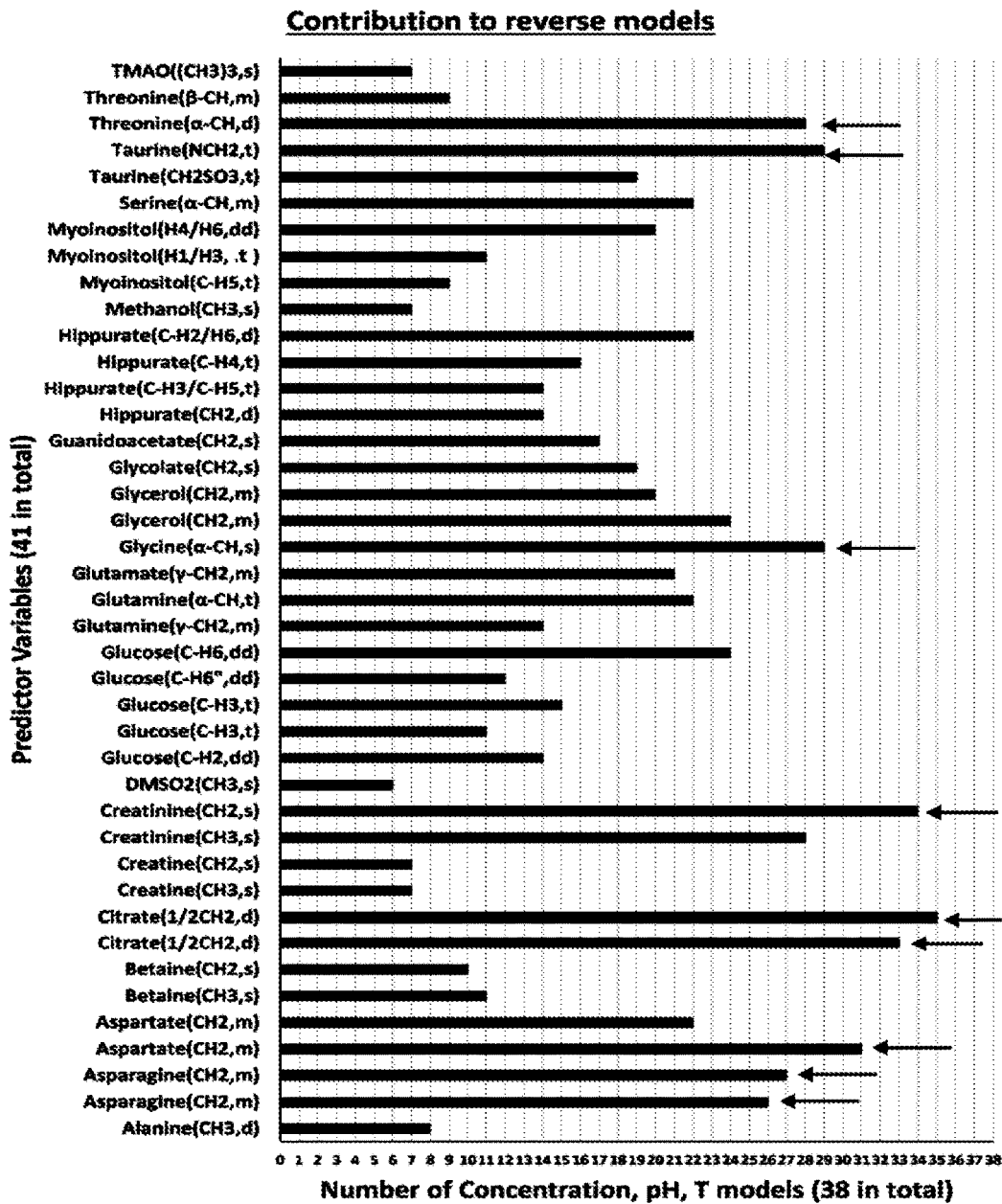
FIG. 3 Variables/chemical shift values (41 $^1$H spin systems NMR chemical shifts) contribution to the 38 metabolite concentrations, pH and T (partial) models. Bars indicate in how many models each variable is weighted (significant) for the fitting. Arrows point out the bars that correspond to the variables that are significant for the highest number of models.
Figure 12:
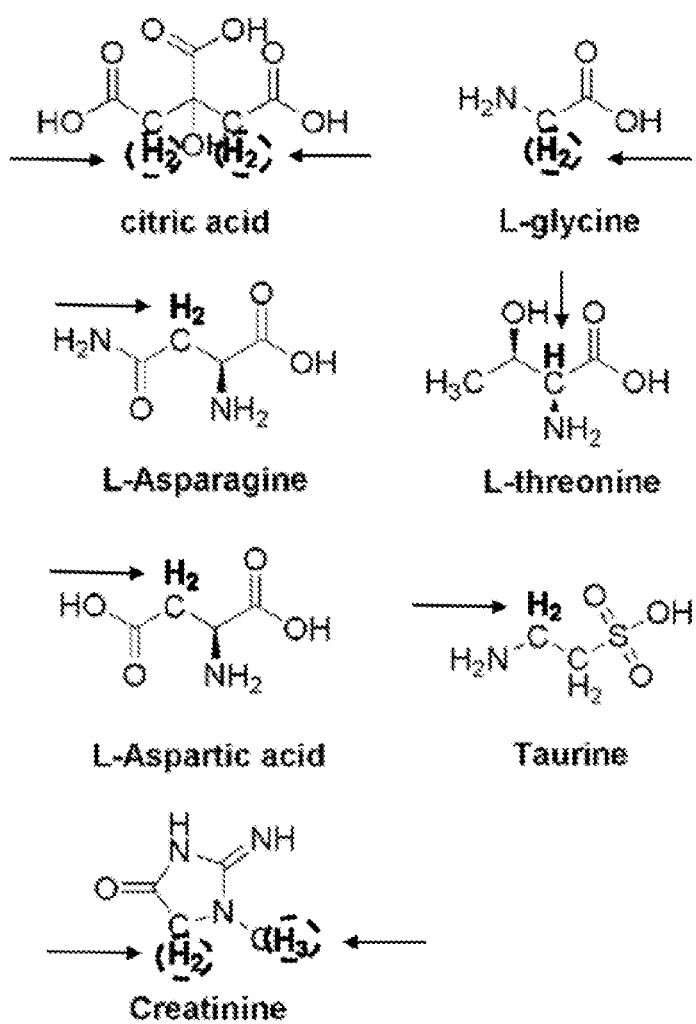

At this point, the implementation requires to build a reverse function that, given the chemical shift values, could reconstruct the concentrations of (molecular) metabolites and ions (ion type metabolites) that were providing those values. The same mathematical approach was employed for the construction of the reverse (partial) models. In this case the response (y) values were the concentrations of each substance/metabolite (including ion), pH and T (i.e. the sample characteristics), whereas the variables were the 41 studied NMR spin systems. The 38 produced (partial) models exhibited lower cross validated $R^2$ values (>0.90) than the $\delta_O$ (partial) models, however reasonably, the ions, creatinine, urea, hippurate, pH and temperature were perfectly fitted ($R^2$>0.98). ANOVA decomposition of the 38 models revealed which $^1$H spin systems NMR signals from the 41 studied could act as "sensors" for the prediction of the matrix of concentrations of the artificial urines. The highest score was exhibited by the $^1$H nuclei of the metabolites highlighted by arrows in FIG. 12 and by arrows in FIG. 3.

In urine, citrate, creatinine as well as glycine are always present in high concentration with respect to other metabolites, and their $^1$H-NMR signals are quite distinctive, allowing for a facile assignment compared to the aspartic acid, asparagine, taurine and threonine NMR signals. Taking under consideration this criterion, the reduction of all concentrations, pH, and T (partial) models took place. The 38 reduced (partial) models were constructed using only 5 variables (i.e. the number of reference NMR systems R is 5 here): the two singlets of creatinine, the two doublets of citrate and the singlet of glycine, which are highlighted in FIG. 12 by dashed circles. Apparently, the cross validated $R^2$ and RMSE values of the new fitted models were worse than those of the full models (see Table 2 for some examples); however the knowledge of the previously mentioned NMR signals positions of the 5 sensors (or reference NMR spin systems) could predict quite sufficiently (as a starting point) the concentration of the (molecular) metabolites and ions (ion metabolites) as well as the pH and T values in each artificial urine mixture via its NMR profile, without using any fitting procedure and/or relying on metabolite NMR signature templates from databases or NMR signals integration.

TABLE 2

| Metabolites concentration, pH and T models (4 examples) | Cross validated $R^2$ (full model) | Cross validated $R^2$ (reduced model) | RMSE (full model) | RMSE (reduced model) |
| --- | --- | --- | --- | --- |
| Chloride ions | 0.99 | 0.98 | 0.07 (mM) | 0.15 (mM) |
| Sulfate Ions | 0.98 | 0.96 | 0.05 (mM) | 0.12 (mM) |
| Creatinine | 0.99 | 0.95 | 0.08 (mM) | 0.28 (mM) |
| pH | 0.99 | 0.95 | 0.02 | 0.04 |

The detection of the 5 sensor NMR signals offered the opportunity to explore the correlation between them and each one of the above mentioned studied NMR signals of the rest of the metabolites. Namely, 36 new $\delta_O$ (partial) models were created (following the same mathematical approach) using the 5 sensor peak positions in the 1235 mixtures as variables (examples of their $R^2$ and RMSE values are reported in Table 3), i.e. the number of non-reference NMR spin systems N is 36 here. The fitted $\delta_O$ reduced (partial) models (functions) showed high $R^2$ and low RMSE values, demonstrating that 36 $^1$H spin systems NMR signals positions could be predicted via the positions of the 5 sensor peak positions.

In conclusion, 4 different types of models (or, to be more exact, sub-models of the model appliance) were created:
i) 2 kinds of full models. The first kind (also referred to as first sub-model of full type) includes the prediction of 41 $^1$H spin systems NMR peaks positions by the knowledge of mixture's substance/metabolite concentrations, pH and T values (38 variables), and the second kind (also referred to as second sub-model of full type) includes the prediction of 36 substance/metabolite concentrations, pH and T through the 41 $^1$H spin systems NMR peaks positions.
ii) 2 kinds of reduced models. The 38 predictive (partial) models of substance/metabolite concentrations, pH and T by the 5 sensor NMR signals positions (together representing a first sub-model of reduced type), and the predictive (partial) models of 36 $^1$H spin systems $\delta_O$ values based upon the 5 sensor NMR peaks positions (together representing a second sub-model of reduced type).

TABLE 3

| $\delta_O$ models (4 examples) | Cross validated $R^2$ (full model) | Cross validated $R^2$ (reduced model) | RMSE (ppm) (full model) | RMSE (ppm) (reduced model) |
| --- | --- | --- | --- | --- |
| Threonine, —CH (d, 3.59 ppm) | 0.99 | 0.98 | 0.0002 | 0.0004 |
| Glycolate, —CH$_2$ (s, 3.95 ppm) | 0.99 | 0.97 | 0.0001 | 0.0003 |
| Aspartate, —CH$_2$ (m, 2.68 ppm) | 0.99 | 0.98 | 0.0002 | 0.0004 |
| Taurine, —CH$_2$SO$_3$ (t, 3.27 ppm) | 0.99 | 0.98 | 0.0001 | 0.0003 |

The combination of the 4 kinds of models (compare FIG. 4) led to the construction of a final algorithm, based upon the best metabolite's NMR signals positions prediction (tested in 60 real urine samples and 20 randomly prepared artificial urine mixtures). The compound concentration predictions are focused only upon the random artificial mixtures, where the substance (metabolite including ion) concentrations were known.

Figure 4:
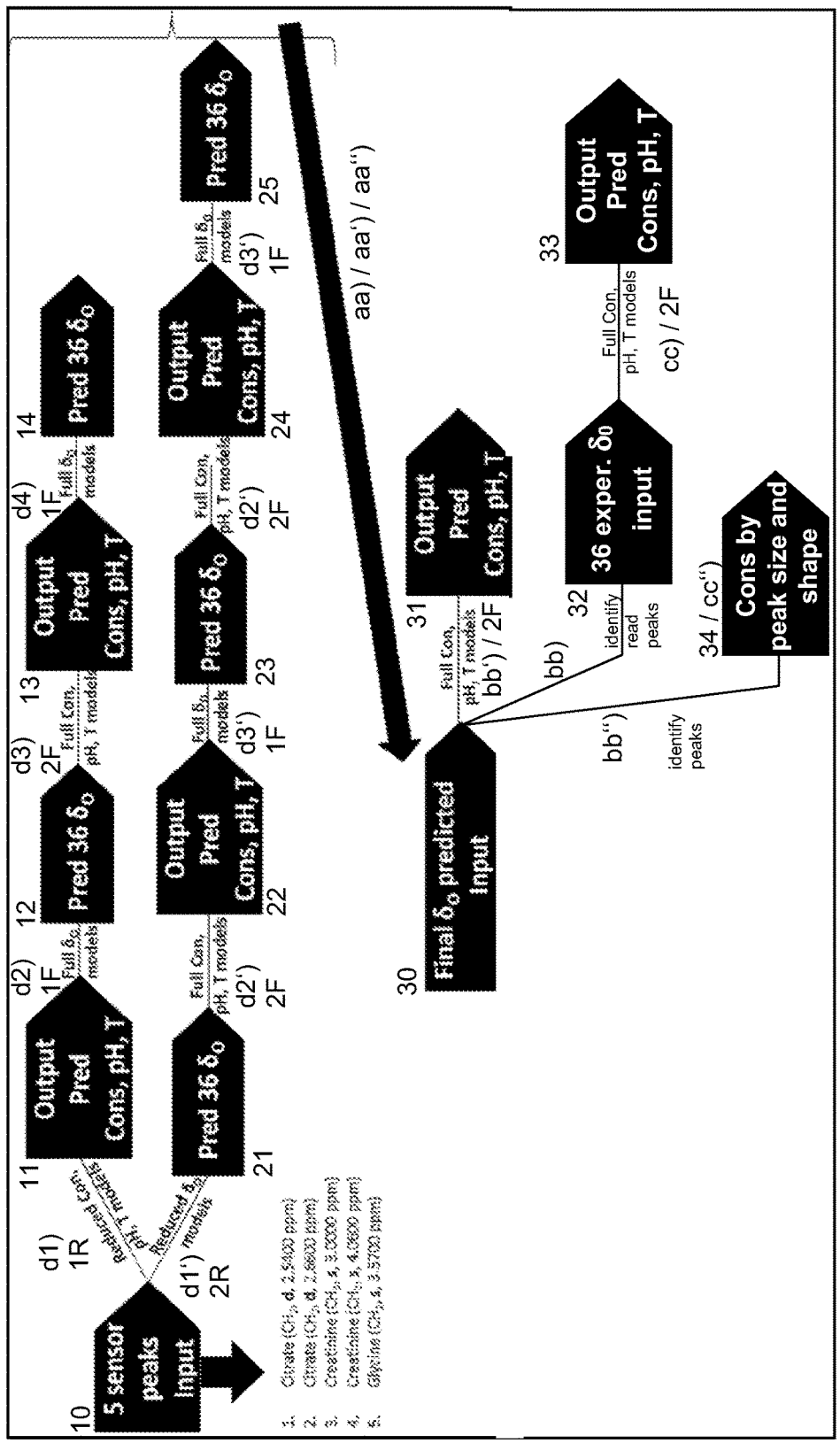
FIG. 4 Workflow of the presented embodiment of the inventive method for predicting chemical shift values, in a variant starting with a first sub-model of reduced type (top line) calculating sample characteristics from experimental chemical shift values of reference NMR spin systems, and in a variant starting with a second sub-model of reduced type (second to top line), calculating predicted chemical shift values from experimental chemical shift values of reference NMR spin systems, and further of three optional subsequent variants for determination of metabolite concentrations.

The final algorithm shown in FIG. 4 can be performed in two variants. In a first variant, shown in the top line, the five sensor peaks (or experimental chemical shift values of reference NMR spin systems) 10 read from the recorded NMR spectrum are fed in a substep d1) into the first sub-model of reduced type 1R, resulting in an output 11 of predicted metabolite concentrations, pH and T values (i.e. here 38 predicted characteristics) for the sample. Upon these predicted characteristics, the first sub-model of full type 1F is applied in a substep d2), thus obtaining an output 12 of 36 predicted chemical shift values $\delta_O$ for the non-reference NMR spin systems. Together with the experimental chemical shift values 10 for the reference NMR spin systems, these are input into the second sub-model of full type 2F in a substep d3), resulting in predicted characteristics 13 again. In a substep d4), these are fed into the first sub-model of full type 1F again to obtain an output 14 of further predicted chemical shift values of second iteration (note that if desired, further iterations of substeps d3) and d4) may be applied). The resulting predicted chemical shift values may be used as final predicted chemical shift values 30.

In a second alternative variant, shown in the line below, the five sensor peaks (or experimental chemical shift values of reference NMR spin systems) 10 read from the recorded NMR spectrum are fed in a substep d1') into the second sub-model of reduced type 2R, resulting in a an output 21 of 36 predicted chemical shift values $\delta_O$ for the non-reference NMR spin systems. Together with the experimental chemical shift values 10 for the reference NMR spin systems, these are input into the second sub-model of full type 2F in a substep d2'), resulting in predicted characteristics 22. In a substep d3'), these are fed into the first sub-model of full type 1F again to obtain an output 23 of further predicted chemical shift values. In the example shown, this output 23 together with the experimental chemical shift values 10 of the reference NMR spin systems are used in a second iteration of substeps d2') and d3'), thus obtaining output 24 of predicted concentrations of second iteration and output 25 of predicted chemical shift values of second iteration (if desired, further iterations of steps d2') and d3') may be applied). The resulting predicted chemical shift values may be used as final predicted chemical shift values 30 again.

For (optional) further determining metabolite concentrations, the previously described algorithm can be considered as a first step aa) or aa') or aa") in which chemical shift values 30 of non-reference NMR spin systems have been determined.

If a quick estimate of metabolite concentrations is desired, with a coarse accuracy being enough, the final predicted chemical shift values 30 of the non-reference NMR spin systems (together with the experimental chemical shift values 10 of the reference NMR spin systems) can be used in a step bb'), applying second sub-model of full type 2F once more, resulting in an output 31 of predicted characteristics, including metabolite concentrations (note that if only specific concentrations are of interest, it may suffice to apply only partial models of the second sub-model of full type 2F). This approach is used further below (compare FIGS. 6-8 in particular) for concentration determination. Note that this procedure may be applied to derive concentrations of NMR inactive metabolites, if desired.

If a somewhat more accurate estimate is desired, but the efforts of peak integration or lineshape fitting are to be avoided, the final predicted chemical shift values 30 can be used to identify the peaks of the non-reference NMR spin systems in the NMR spectrum, and read out their experimental chemical shift values in a step bb). This input 32 may be used in a step cc) applying the second sub-model of full type 2F once more to obtain an output 33 of predicted characteristics, including metabolite concentrations (again note that if only specific concentrations are of interest, it may suffice to apply only partial models of the second sub-model of full type 2F). Note that this procedure may be applied to derive concentrations of NMR inactive metabolites, too, if desired.

Finally, if a high accuracy of compound (or NMR active metabolite) concentration is desired, the final predicted chemical shift values 30 can be used to identify the peaks of at least one (non-reference) NMR spin system of the compound in the NMR spectrum in a step bb"), and to derive concentration information from the size and shape of the identified peak (or peaks) 34, e.g. by peak integration or lineshape fitting.

EXAMPLE

A) Artificial Urine Mixture Tests.

Twenty artificial urine mixtures were produced, containing random substance/metabolite (molecular and ion) concentration values (calculated by a randomizer) and pH values, and their NMR spectra were acquired at different temperatures. All random values were within the limits of concentration, pH and T matrix of the applied models. In the 20 NMR spectra the 5 sensor signals lied inside the chemical shifts matrix limits.

Figure 5:
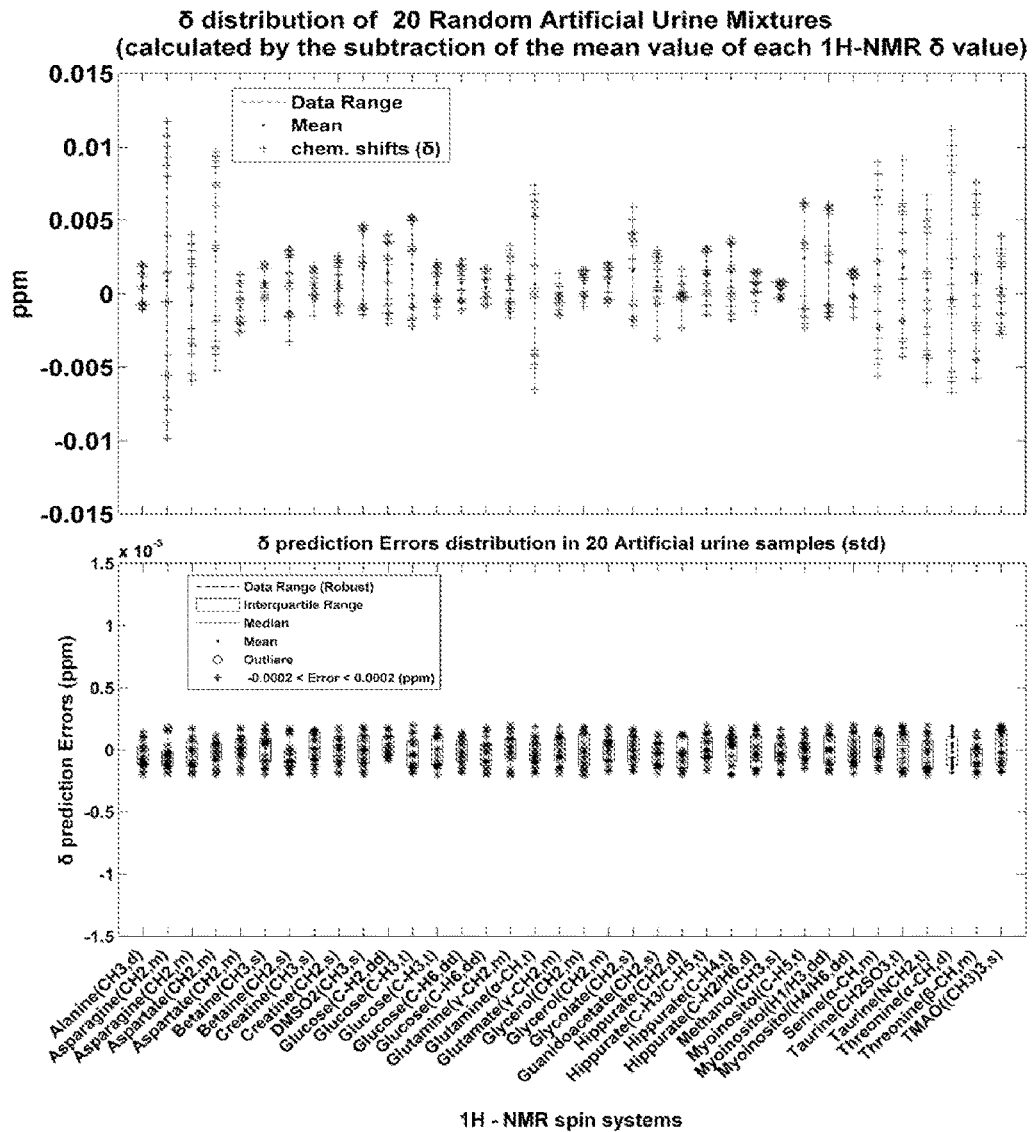
FIG. 5 Chemical shifts distributions in 20 randomly prepared artificial urine mixtures (top figure) and their corresponding predictions errors distribution in the presented embodiment of the inventive method.

The $\delta_O$ prediction errors distribution is summarized in FIG. 5, where, as shown, the prediction accuracy is almost perfect. Namely, all 36 predicted $^1$H spin systems NMR positions exhibit less or equal to ±0.0002 ppm error. Although the small errors are produced from artificial and not real urine samples, they validate the chosen mathematical-algorithmic approach for NMR peak position predictions.

Figure 6:
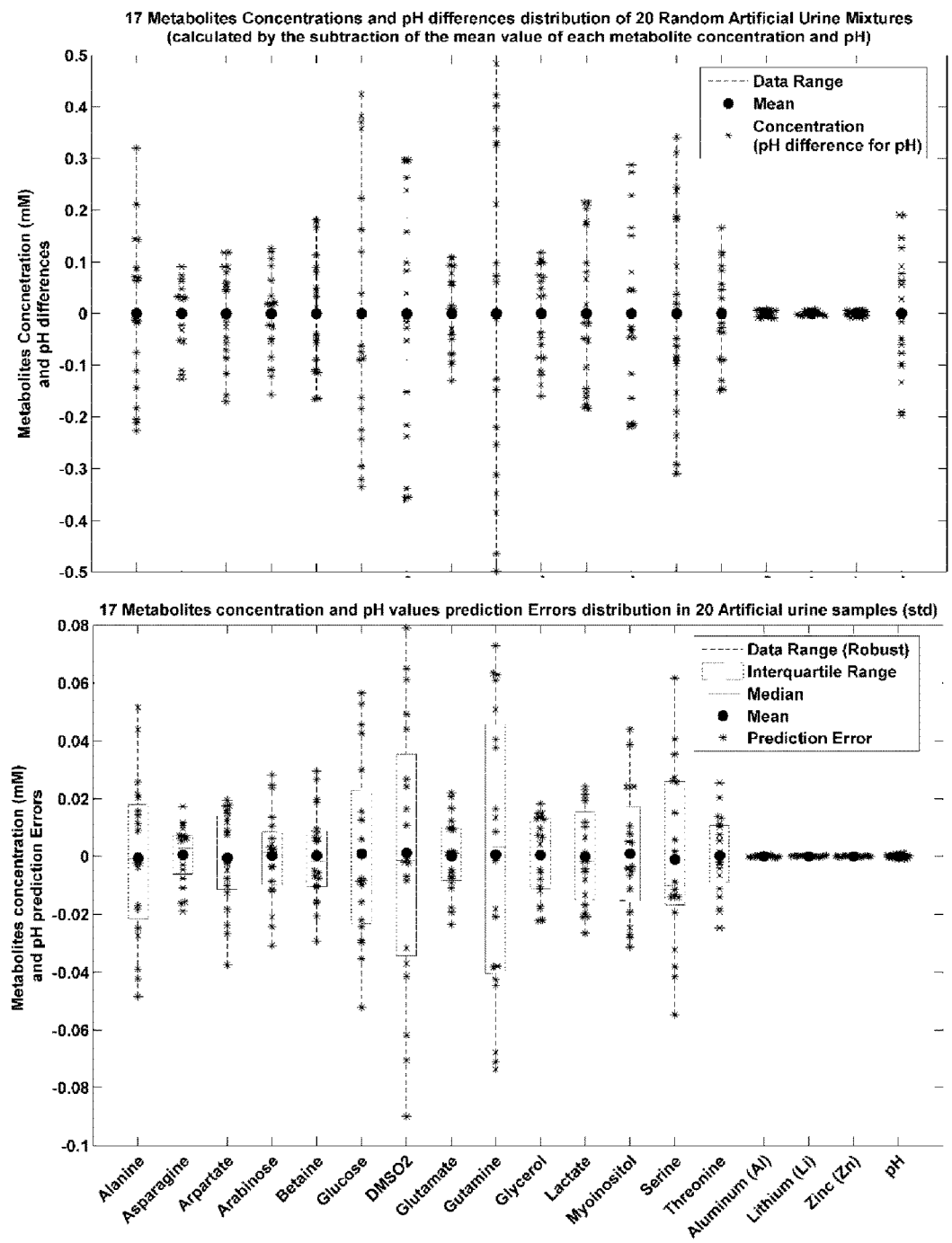
Figure 7:
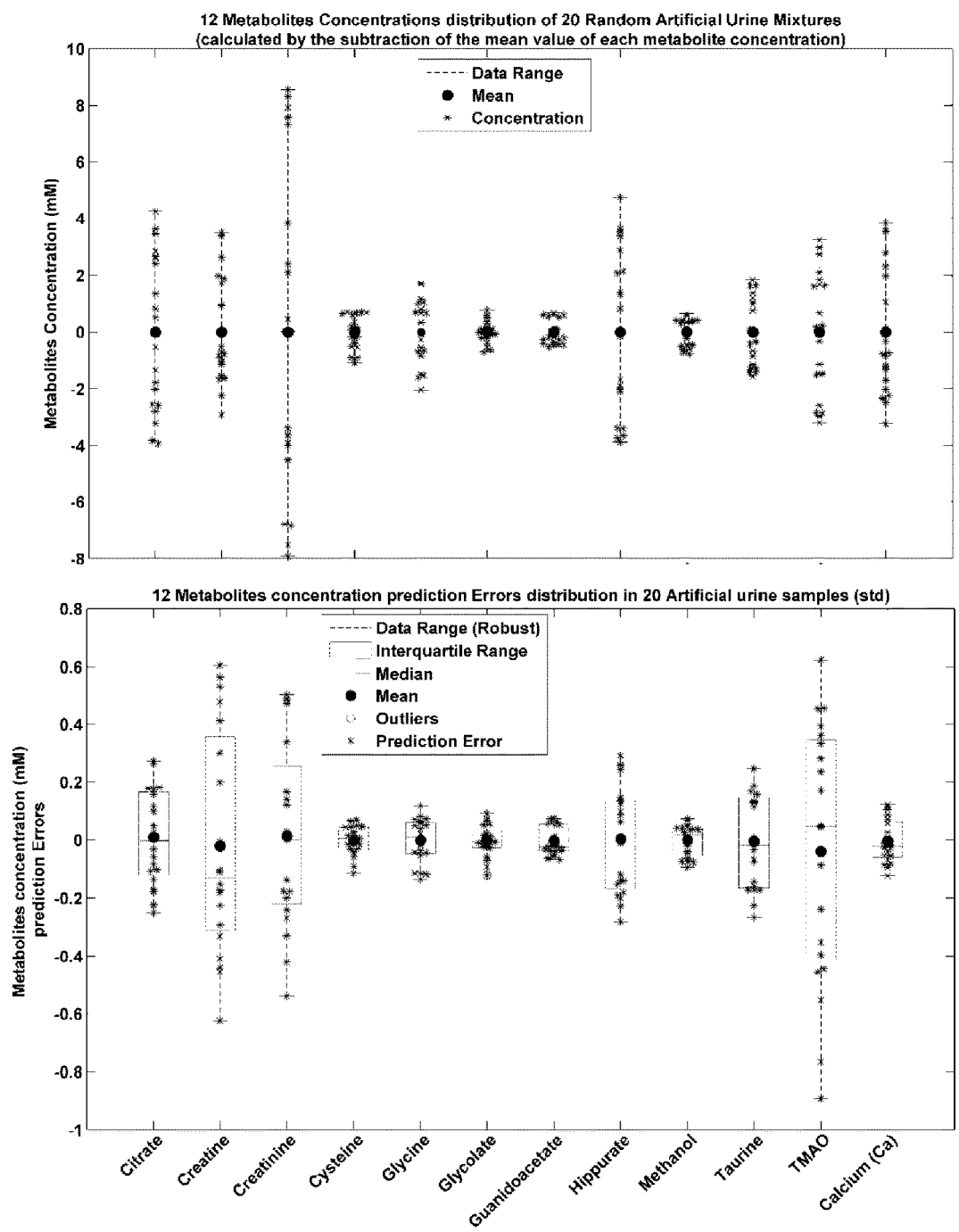
FIG. 7 12 metabolites concentrations distributions in 20 randomly prepared artificial urine mixtures (top figure) and their corresponding predictions errors distribution in the presented embodiment of the inventive method.
Figure 8:
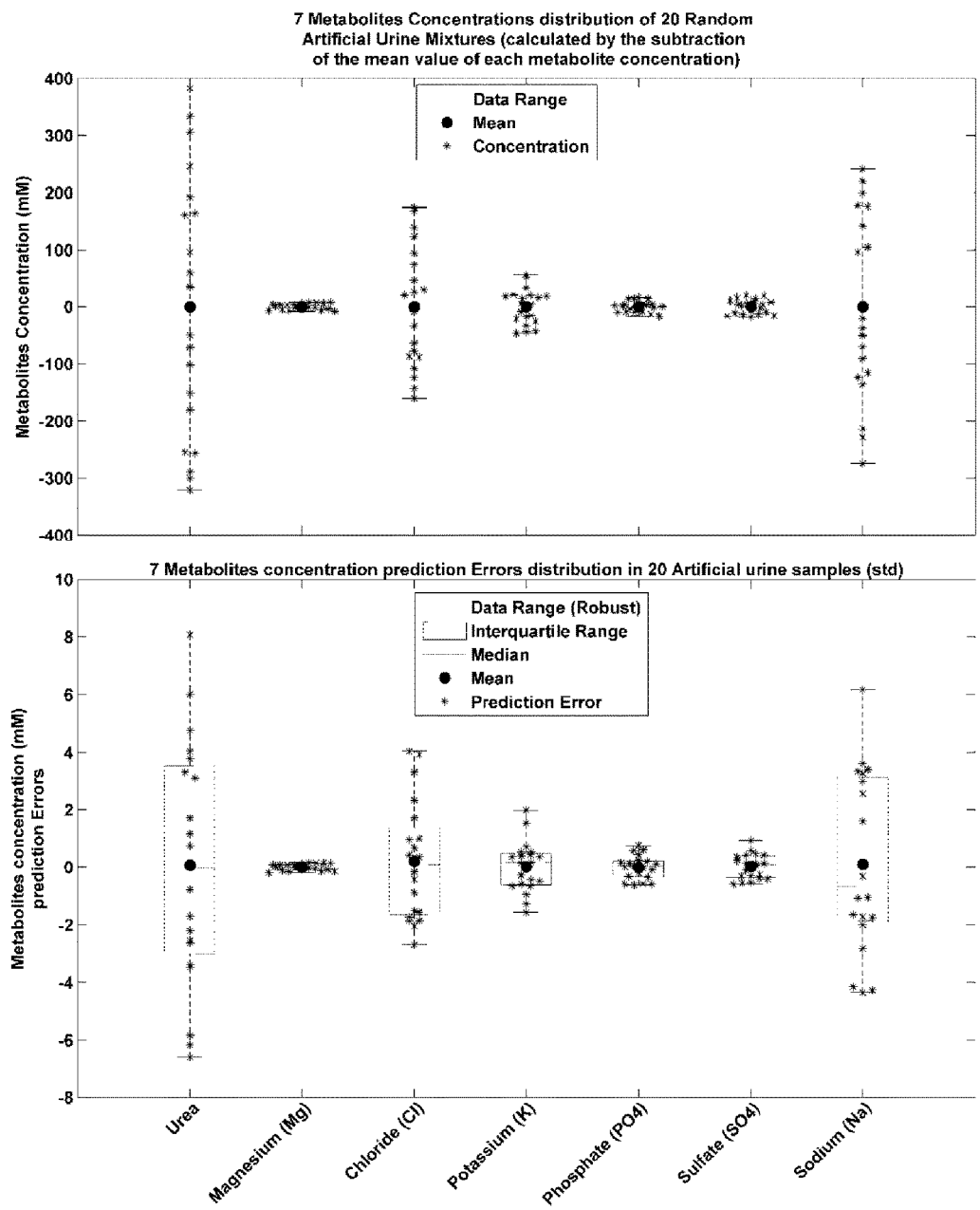

Further, all ion, creatinine, hippurate, aspartate, asparagine and urea concentrations, pH and T predictions exhibited less than 2-4% relative errors, whereas all other metabolite concentrations were predicted with 5-15% relative errors. As depicted in FIGS. 6-8, the relative prediction errors distribution of the metabolites concentrations and pH is very small compared to the large distribution of the metabolites concentrations in the twenty artificial urine test mixtures. Namely, the presented algorithm could provide information of the urine sample metabolites concentrations range, without any NMR signals integration-deconvolution.

B) Tests on Real Urine Samples.

Sixty different real urine samples were selected for automatic signal prediction on condition that the 5 sensor chemical shifts (or experimental chemical shift values of the reference NMR systems) constituting the input file of the algorithm lied inside the limits of the chemical shifts matrix of the presented embodiment. This criterion was set because the model extrapolation efficiency is low, especially when the 5 values of the input file are very far from the chemical shifts matrix upper-lower limits. This limitation of the presented algorithm is due to the fact that it was constructed and trained by quite narrow metabolite/substance concentrations (bibliographic low and mean values), pH (6.8-7.2) ranges (note that for broader ranges of the teaching database, this limitation is overcome).

Figure 9:
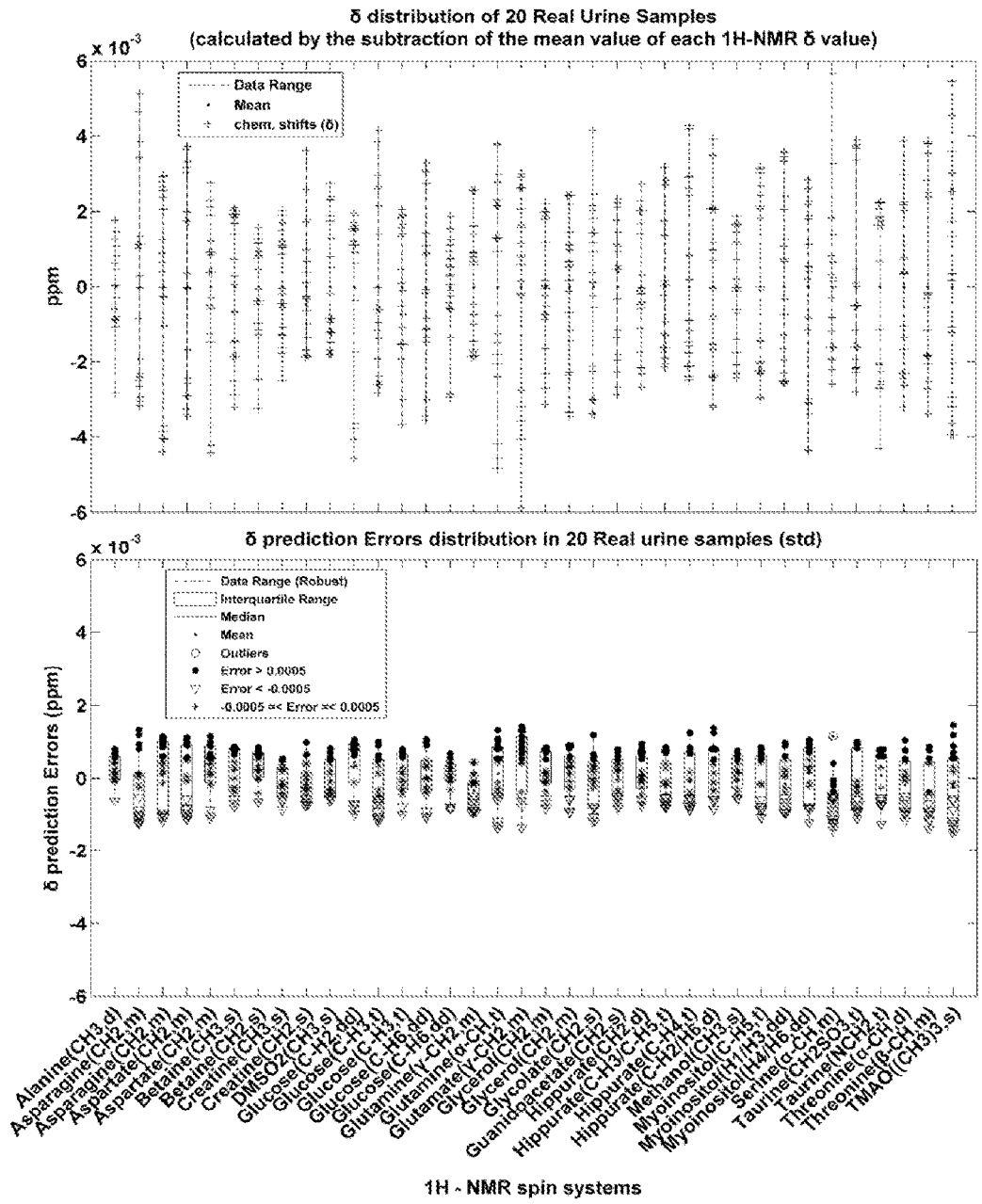
FIG. 9 Chemical shifts distribution in 20 real urine samples (top figure) and their corresponding predictions errors distribution in the presented embodiment of the inventive method.
Figure 10:
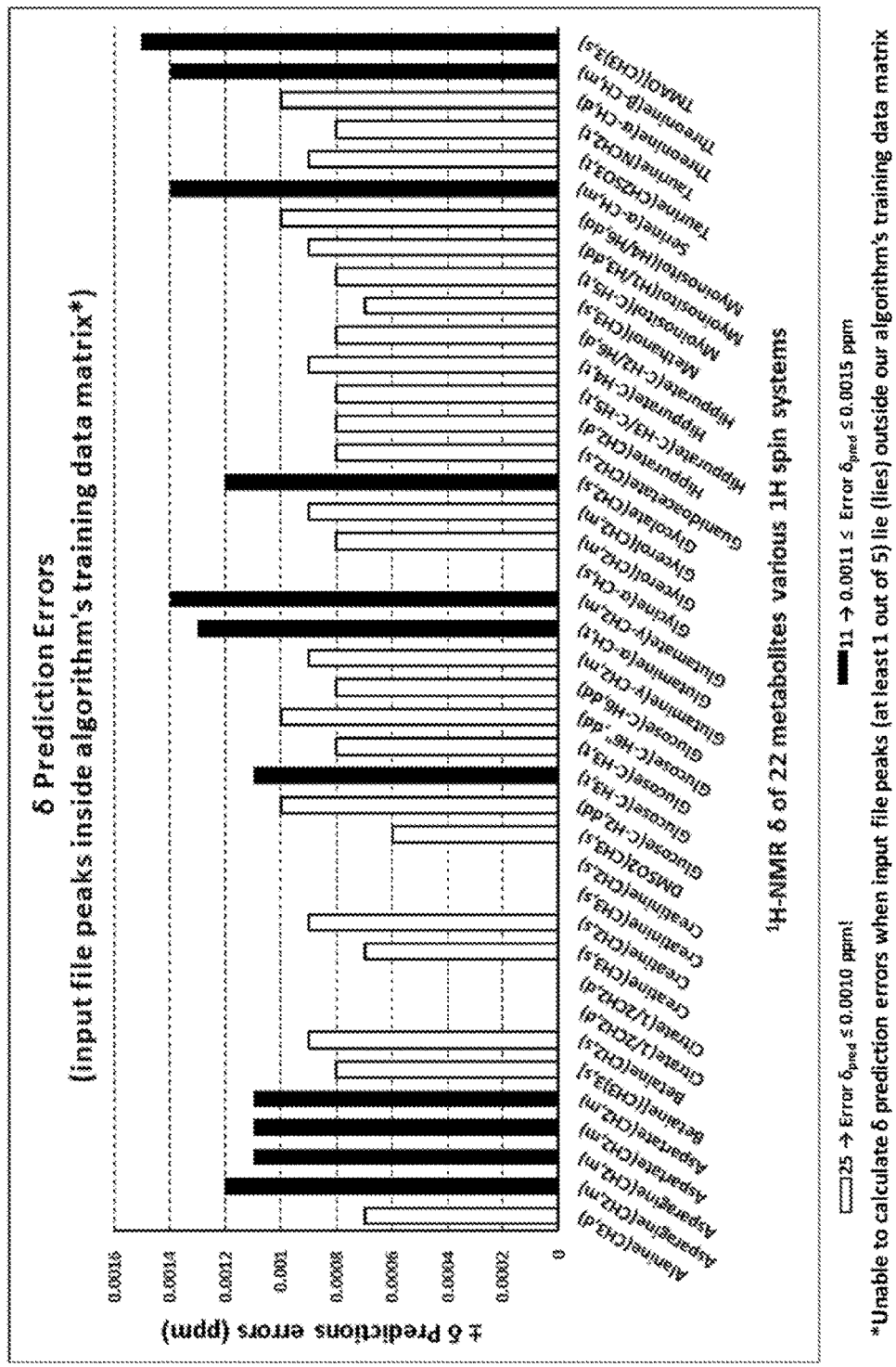
FIG. 10 δ prediction errors of 36 $^1$H spin systems in 60 real urine biofluids samples in the presented embodiment of the inventive method.
Figure 11:
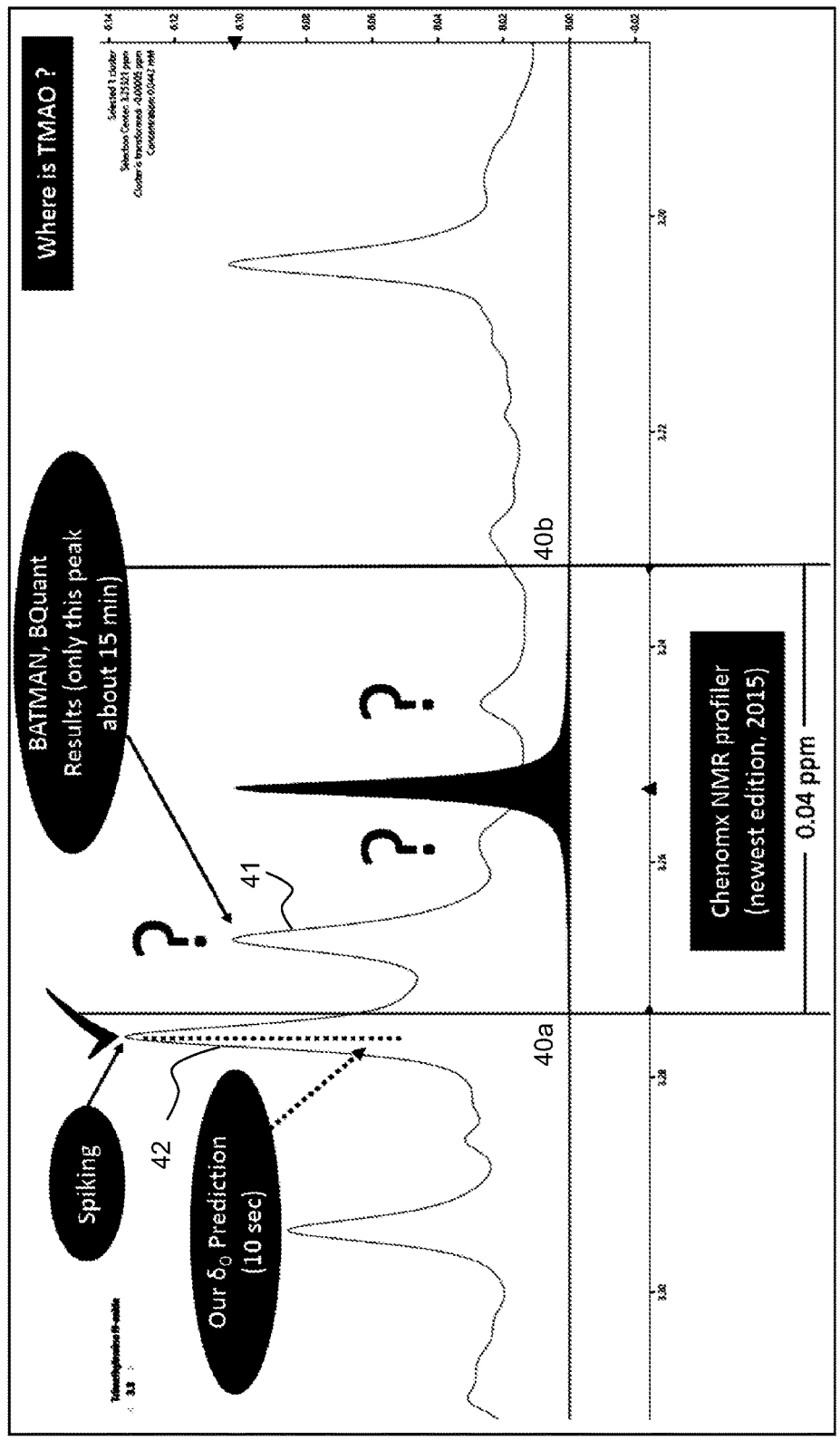
FIG. 11 TMAO $^1$H-NMR peak assignment by the presented embodiment of the inventive method, BQuant, BATMAN and Chenomx NMR profiler.

FIG. 9 depicts the $\delta_O$ prediction errors distribution of 20 out of the 60 real urine samples which exhibited the highest errors distribution, and FIG. 10 summarizes the absolute prediction errors from all 60 real urine biofluids. The $\delta_O$ prediction errors are ≤|0.0015| ppm, which—considering the used artificial urine metabolites mixtures formation—are more than satisfying. According to other semi-automatic targeted metabolite detection methods from 1D $^1$H-NMR biofluids spectra (for example Bayesian approaches error: ≤|0.0020|) the algorithm's $\delta_O$ predictions already exhibits lower error ranges. A comparison example is demonstrated in FIG. 11, where the inquiry is the assignment of TMAO metabolite in a healthy person's urine NMR profile. The NMR spectrum is loaded on the Chenomx NMR profiler console, 2015 edition. The manual assignment (by Chenomx) prompts the user to search the spectral range that is defined by the vertical lines 40a, 40b. In this relatively large spectral region (0.04 ppm) 3 peaks (marked by "?") are candidates for the TMAO's $^1$H-NMR singlet. The use of BQuant and BATMAN software for the assignment and quantification of TMAO (given the region 3.26-3.30 ppm) took about 15-20 min and their assignment result was the NMR peak 41 pointed by the right arrow. Our automated algorithm's $^1$H-NMR TMAO (($CH_3$)$_3$NO) $\delta_O$ prediction (performed in 10 sec) is pointed by the dotted vertical line and arrow.

The correct TMAO's $^1$-NMR peak 42 according to the spiking result is pointed by the left arrow and the tick symbol. All automated approaches (except the inventive one) exhibited a false positive result, whereas the invention's prediction error was +0.0002 ppm, calculated within a few seconds by the use of an average laptop.

The inventive method allows fast $\delta_O$ "accurate" predictions (so far ≤|0.0015| ppm); further a fast prediction of ion concentration (by NMR) and of other metabolite concentrations, pH and temperature, are feasible with very small relative error (≤2%) by mathematical procedures and no metabolite NMR pattern fitting procedures. The method has, in practice, no need for high computational power. The method is well suited for a totally automated procedure. There is no need for a specific NMR protocol like specific NMR spectrum resolution, number of scans or even specific sample preparation protocol with specific buffer capacity. Only TSP as a reference compound is needed.

Materials and Experimental Methods of the Example

1) NMR Sample Preparation.

The 26 urine (molecular) metabolites were purchased by Sigma. These metabolites are listed in Table 4 as well as the salts from which the 10 studied ions were extracted. 10% of common urine buffer was used in each NMR sample final volume. The buffer contains 1.5 M $KH_2PO_4$, 2 mM $NaN_3$ and 0.1% TSP as NMR reference compound which are dissolved in $D_2O$, 99.8% $^2H$. The pH of the NMR samples was adjusted by the addition of HCl or NaOH solutions of 4 N concentration and measured by a pH meter at 298 K.

TABLE 4

List of the metabolites and ions used in the artificial urine mixtures.

| Metabolites | Salts (Ions) |
|---|---|
| L-Alanine | $Na_2SO_4$ |
| L-Asparagine | NaCl |
| L-Aspartic acid | LiCl |
| L-Arabinose | $AlCl_3$ |
| Betaine | KCl |
| Citrate | $Na_3PO_4$ |
| Creatine | $MgCl_2$ |
| Creatinine | $CaCl_2$ |
| L-Cysteine | $ZnCl_2$ |
| D-Glucose | |
| Dimethyl Sulfone | |
| L-Glutamic acid | |
| L-Glutamine | |
| Glycerol | |
| L-Glycine | |
| Glycolic acid | |
| Guanidoacetic acid | |
| Hippuric acid | |
| Lactate | |
| Methanol | |
| Myoinositol | |
| L-Serine | |
| Taurine | |
| L-Threonine | |
| TMAO | |
| Urea | |

2) NMR Experiments

One dimensional (1D) 1H-NMR spectra for all samples were acquired using a Bruker 600 MHz spectrometer (Bruker BioSpin) operating at 600.13 MHz proton Larmor frequency and equipped with a 5 mm CPTI 1H-13C/31P-2H cryo-probe including a z-axis gradient coil, an automatic tuning—matching (ATM) and an automatic sample changer. A PT 100 thermocouple provided temperature stabilization at the level of approximately 0.1 K at the sample. Before measurement, samples were kept for at least 3 min inside the NMR probehead, for temperature equilibration. A one-dimensional NMR spectrum was acquired with water peak suppression using a standard pulse sequence (NOESYpresat, Bruker), using 64 free induction decays (FIDs), 64 k data point, a spectral width of 12,019 Hz, an acquisition time of 2.7 s, a relaxation delay of 4 s, and a mixing time of 100 ms. The NOESYpresat pulse sequence is the standard for metabolomic analysis (Aranjbar, Ott, Roongta, & Mueller, 2006) since it provides very good water suppression together with quantitative information as demonstrated in Saude, Slupsky, and Sykes (2006).

3) Computational Platforms

The algorithm was developed in MATLAB R2014a computing environment and needs MATLAB for its application. All MARS models-functions were produced by the use of free available ARESlab toolbox (Jekabsons G., ARESLab: Adaptive Regression Splines toolbox for Matlab/Octave, 2015, available at http://www.cs.rtu.lv/jekabsons/). All other features of the algorithm were developed by the inventors.

REFERENCES

1. Holmes, E. et al. Human metabolic phenotype diversity and its association with diet and blood pressure. *Nature* 453, 396-400 (2008).
2. Weckwerth, W., Loureiro, M. E., Wenzel, K. & Fiehn, O. Differential metabolic networks unravel the effects of silent plant phenotypes. *Proc. Natl. Acad. Sci. United States Am.* 101 , 7809-7814 (2004).
3. Larive, C. K., Jr., G. A. B. & Dinges, M. M. NMR Spectroscopy for Metabolomics and Metabolic Profiling. *Anal. Chem.* 87, 133-146 (2015).
4. Astle, W., De Iorio, M., Richardson, S., Stephens, D. & Ebbels, T. A Bayesian Model of NMR Spectra for the Deconvolution and Quantification of Metabolites in Complex Biological Mixtures. *J. Am. Stat. Assoc.* 107, 1259-1271 (2012).
5. Gómez, J. et al. Dolphin: A tool for automatic targeted metabolite profiling using 1D and 2D 1H-NMR data. *Anal. Bioanal. Chem.* 406, 7967-7976 (2014).
6. Hao, J. et al. Bayesian deconvolution and quantification of metabolites in complex 1D NMR spectra using BATMAN. *Nat. Protoc.* 9, 1416-27 (2014).
7. Jiang, L., Huang, J., Wang, Y. & Tang, H. Eliminating the dication-induced intersample chemical-shift variations for NMR-based biofluid metabonomic analysis. *Analyst* 137, 4209-4219 (2012).
8. Emwas, A.-H. et al. Standardizing the experimental conditions for using urine in NMR-based metabolomic studies with a particular focus on diagnostic studies: a review. *Metabolomics* 11, 872-894 (2014).
9. Wishart, D. S. et al. HMDB: the Human Metabolome Database. *Nucleic Acids Res.* 35 , D521-D526 (2007).
10. Bouatra, S. et al. The human urine metabolome. *PLoS One* 8, e73076 (2013).
11. Ravanbakhsh, S. et al. Accurate, Fully-Automated NMR Spectral Profiling for Metabolomics. *PLoS One* 10, e0124219 (2015).
12. Xia, J., Bjorndahl, T. C., Tang, P. & Wishart, D. S. MetaboMiner—semi-automated identification of metabolites from 2D NMR spectra of complex biofluids. *BMC Bioinformatics* 9, 1-16 (2008).
13. Zheng, C., Zhang, S., Ragg, S., Raftery, D. & Vitek, O. Identification and quantification of metabolites in 1H NMR spectra by Bayesian model selection. *Bioinformatics* 27, 1637-1644 (2011).
14. Wishart, D. S. et al. HMDB: a knowledgebase for the human metabolome. *Nucleic Acids Res.* 37, D603-10 (2009).
15. Athersuch, T. J., Malik, S., Weljie, A., Newton, J. & Keun, H. C. Evaluation of 1 H NMR Metabolic Profiling Using Biofluid Mixture Design. *Anal. Chem.* 85, 6674-6681 (2013).
16. Sokolenko, S. et al. Profiling convoluted single-dimension proton NMR spectra: A plackett-burman approach for assessing quantification error of metabolites in complex mixtures with application to cell culture. *Anal. Chem.* 86, 3330-3337 (2014).
17. Friedman, J. H. Multivariate adaptive regression splines. *Ann. Stat.* 19, 1-141 (1991).

What is claimed is:

1. A method for predicting chemical shift values of nuclear magnetic resonance (NMR) spin systems belonging to compounds contained in a sample of a fluid class using NMR spectroscopy comprising:
  a) providing a model appliance representing an information of correlation between captured characteristics of the fluid class, wherein the captured characteristics include concentrations of captured substances contained in the fluid class, and chemical shift values of captured NMR spin systems belonging to compounds contained in the fluid class, wherein the compounds are among the captured substances, wherein the model appliance comprises defined reference NMR spin systems, wherein the reference NMR spin systems are a subset of the captured NMR spin systems, and wherein the reference NMR spin systems belong to compounds which are omnipresent in the fluid class, wherein the model appliance is derived from a teaching database, the teaching database comprising for each of
a plurality of teaching samples of the fluid class
values of the captured characteristics, including values for the concentrations of the captured substances, and chemical shift values of the captured NMR spin systems, obtained through use of a teaching NMR spectrum recorded of the respective teaching sample and assignment of peaks in the teaching NMR spectrum to the captured NMR spin systems and determining the chemical shift values of the peaks,
and wherein the model appliance is based on correlation functions for the chemical shift values and the captured characteristics;

b) recording an NMR spectrum of the sample of the fluid class;

c) identifying peaks in the recorded NMR spectrum which belong to the defined reference NMR spin systems of the model appliance, and determining experimental chemical shift values of the peaks from the recorded NMR spectrum; and d) predicting a chemical shift value of at least one of the captured NMR spin systems not belonging to the reference NMR spin systems by applying the model appliance onto the experimental chemical shift values of the reference NMR spin systems.

2. The method according to claim 1, wherein the reference NMR spin systems are chosen from a subset of the captured NMR spin systems for which the chemical shift values are of significance for an above-average amount of the concentrations of the captured substances, as determined by the model appliance.

3. The method according to claim 1, wherein the reference NMR spin systems are determined using a statistical correlation analysis method selected from the group consisting of: an Analysis of Variance (ANOVA) decomposition, a Spearman's rank correlation, a Kendall's Rank correlation, a spurious correlation analysis, and a canonical correlation analysis.

4. The method according to claim 1, wherein the model appliance comprises a 1R sub-model of reduced type which indicates the captured characteristics $x_j$ as a function f of the chemical shift values $\delta_i$ of the reference NMR spin systems only, with $$x_j = f_j(\delta_1, \ldots, \delta_R),$$

with j: index of captured characteristics, with j=1, ..., C and C: number of captured characteristics, and with i: index of reference NMR spin systems, with i=1, ..., R and R: number of reference NMR spin systems.

5. The method according to claim 4, wherein the model appliance comprises a 1F sub-model of full type which indicates the chemical shift values $\delta_1$ of the non-reference NMR spin systems or all captured NMR spin systems, as a function f of the captured characteristics $x_j$, with $$\delta_l = f_l(x_1, \ldots, x_C),$$

with l: index of NMR spin systems, with l=1, ..., N and N: number of non-reference NMR spin systems or with l=1, ..., S and S: number of all captured NMR spin systems, and with j: index of captured characteristics, with j=1, ..., C and C: number of captured characteristics; and wherein the model appliance comprises a 2F sub-model of full type which indicates the characteristics $x_j$ as a function f of the chemical shift values $\delta_1$ of the captured NMR spin systems, with $$x_j = f_j(\delta_1, \ldots, \delta_S),$$

with j: index of captured characteristics, with j=1, ..., C and C: number of captured characteristics, and wih l: index of captured NMR spin systems, with l=1, ..., S and S: number of captured NMR spin systems.

6. The method according to claim 5, further comprising:

d1) applying the 1R sub-model of reduced type onto the experimental chemical shift values of the reference NMR spin systems to obtain predicted characteristics;

d2) applying the 1F sub-model of full type onto the predicted characteristics obtained in previous substep d1) to obtain predicted chemical shift values of the non-reference NMR spin systems;

d3) applying the 2F sub-model of full type onto the experimental chemical shift values of the reference NMR spin systems and the predicted chemical shift values of the non-reference NMR spin systems obtained in previous substep d2) to obtain predicted characteristics;

d4) applying the 1F sub-model of full type onto the predicted characteristics obtained in previous substep d3) to obtain predicted chemical shift values of the non-reference NMR spin systems.

7. The method of claim 6, starting with the predicted chemical shift values of the non-reference NMR spin systems of substep d4), and further comprising iteratively repeating:

applying the 2F sub-model of full type onto the experimental chemical shift values of the reference NMR spin systems and the predicted chemical shift values of the non-reference NMR spin systems to obtain predicted characteristics;

applying the 1F sub-model of full type onto the predicted characteristics to obtain predicted chemical shift values of the non-reference NMR spin systems.

8. The method according to claim 1, wherein the model appliance comprises a 2R sub-model of reduced type which indicates the chemical shift values $\delta_k$ of the non-reference NMR spin systems as a function f of the chemical shift values $\delta_i$ of the reference NMR spin systems only, with $$\delta_k = f_k(\delta_1, \ldots, \delta_R),$$

with k: index of non-reference NMR spin systems, with k=1, ..., N and N: number of captured non-reference NMR spin systems, and with i: index of reference NMR spin systems, with i=1, ..., R and R: number of reference NMR spin systems.

9. The method according to claim 8, wherein the model appliance comprises a 1F sub-model of full type which indicates the chemical shift values $\delta_1$ of the non-reference NMR spin systems or all captured NMR spin systems, as a function f of the captured characteristics $x_j$, with $$\delta_l = f_l(x_1, \ldots, x_C),$$

with l: index of NMR spin systems, with l=1, ..., N and N: number of non-reference NMR spin systems or with l=1, . . . , S and S: number of all captured NMR spin systems, and with j: index of captured characteristics, with j=1, . . . , C and C: number of captured characteristics; and wherein the model appliance comprises a 2F sub-model of full type which indicates the characteristics $x_j$ as a function f of the chemical shift values $\delta_l$ of the captured NMR spin systems, with $$x_j = f_j(\delta_1, \ldots, \delta_S),$$

with j: index of captured characteristics, with j=1, . . . , C and C: number of captured characteristics, and with l: index of captured NMR spin systems, with l=1, . . . , S and S: number of captured NMR spin systems.

10. The method according to claim 9, further comprising:
d1') applying the 2R sub-model of reduced type onto the experimental chemical shift values of the reference NMR spin systems to obtain predicted chemical shift values of the non-reference NMR spin systems;
d2') applying the 2F sub-model of full type onto the experimental chemical shift values of the reference NMR spin systems and the predicted chemical shift values of the non-reference NMR spin systems obtained in previous substep d1') to obtain predicted characteristics;
d3') applying the 1F sub-model of full type onto the predicted characteristics obtained in previous substep d2') to obtain predicted chemical shift values of the non-reference NMR spin systems.

11. The method of claim 10, starting with the predicted chemical shift values of the non-reference NMR spin systems of substep d3'), and further comprising iteratively repeating:
applying the 2F sub-model of full type onto the experimental chemical shift values of the reference NMR spin systems and the predicted chemical shift values of the non-reference NMR spin systems to obtain predicted characteristics;
applying the 1F sub-model of full type onto the predicted characteristics to obtain predicted chemical shift values of the non-reference NMR spin systems.

12. The method according to claim 1, wherein the model appliance comprises a 1F sub-model of full type which indicates the chemical shift values $\delta_l$ of the non-reference NMR spin systems or all captured NMR spin systems, as a function f of the captured characteristics $x_j$, with $$\delta_l = f_l(x_1, \ldots, x_C),$$

with l: index of NMR spin systems, with l=1, . . . , N and N: number of non-reference NMR spin systems or with l=1, . . . , S and S: number of all captured NMR spin systems, and
with j: index of captured characteristics, with j=1, . . . , C and C: number of captured characteristics.

13. The method according to claim 1, wherein the model appliance comprises a 2F sub-model of full type which indicates the characteristics $x_j$ as a function f of the chemical shift values $\delta_l$ of the captured NMR spin systems, with $$x_j = f_j(\delta_1, \ldots, \delta_S),$$

with j: index of captured characteristics, with j=1, . . . , C and C: number of captured characteristics, and with l: index of captured NMR spin systems, with l=1, . . . , S and S: number of captured NMR spin systems.

14. The method according to claim 1, wherein the captured characteristics include a sample temperature (T), and wherein, for each set of the concentrations of substances, teaching samples of at least two different sample temperatures (T) are included.

15. The method according to claim 1, wherein the model appliance, or at least one sub-model (1R, 2R, 1F, 2F) of the model appliance, is derived from the teaching database through use of a multivariate statistical algorithm, and wherein the multivariate statistical algorithm is a self-learning algorithm.

16. The method according to claim 1, wherein the fluid class is chosen as a biofluid, and wherein the captured substances are metabolites.

17. The method according to claim 16, wherein the biofluid is selected from urine, blood serum, sweat, saliva, cerebrospinal fluid (CSF), or another body fluid, or is selected from fruit juice, chyle, nectar, or another plant fluid.

18. The method according to claim 1, wherein the fluid class is selected from wine, honey, condiments, a plant derived product, or a naturally derived product.

19. A method for determining a concentration of at least one substance contained in a sample of a fluid class by NMR spectroscopy comprising:
a) providing a model appliance representing an information of correlation between captured characteristics of the fluid class, wherein the captured characteristics include concentrations of captured substances contained in the fluid class, and chemical shift values of captured NMR spin systems belonging to compounds contained in the fluid class, wherein the compounds are among the captured substances,
wherein the model appliance comprises defined reference NMR spin systems, wherein the reference NMR spin systems are a subset of the captured NMR spin systems, and wherein the reference NMR spin systems belong to compounds which are omnipresent in the fluid class,
wherein the model appliance is derived from a teaching database, the teaching database comprising for each of a plurality of teaching samples of the fluid class
values of the captured characteristics, including values for the concentrations of the captured substances,
and chemical shift values of the captured NMR spin systems, obtained through use of a teaching NMR spectrum recorded of the respective teaching sample and assignment of peaks in the teaching NMR spectrum to the captured NMR spin systems and determining the chemical shift values of the peaks,
and wherein the model appliance is based on correlation functions for the chemical shift values and the captured characteristics;
b) recording an NMR spectrum of the sample of the fluid class;
c) identifying peaks in the recorded NMR spectrum which belong to the defined reference NMR spin systems of the model appliance, and determining experimental chemical shift values of the peaks from the recorded NMR spectrum; and
aa) predicting chemical shift values of non-reference NMR spin systems of the captured NMR spin systems by applying the model appliance onto the experimental chemical shift values of the reference NMR spin systems;
bb) identifying peaks in the recorded NMR spectrum which belong to the non-reference NMR spin systems through use of the predicted chemical shift values, and determining experimental chemical shift values of the peaks from the recorded NMR spectrum;

cc) calculating the concentration of the at least one substance by applying the model appliance onto the experimental chemical shift values of the reference NMR spin systems and non-reference NMR spin systems, by applying a 2F sub-model of full type which indicates the characteristics $x_j$ as a function f of the chemical shift values $\delta_l$ of the captured NMR spin systems, with $x_j=f_j(\delta_1, \ldots, \delta_S)$, with j: index of captured characteristics, with j=1, ..., C and C: number of captured characteristics, and with l: index of captured NMR spin systems, with l=1, ..., S and S: number of captured NMR spin systems.

20. A method according to claim 19, wherein the at least one substance, the concentration of which is determined by NMR spectroscopy, comprises an ion or other NMR inactive substance.

21. A method for determining a concentration of at least one substance contained in a sample of a fluid class by NMR spectroscopy comprising:
   a) providing a model appliance representing an information of correlation between captured characteristics of the fluid class, wherein the captured characteristics include concentrations of captured substances contained in the fluid class, and chemical shift values of captured NMR spin systems belonging to compounds contained in the fluid class, wherein the compounds are among the captured substances,
      wherein the model appliance comprises defined reference NMR spin systems, wherein the reference NMR spin systems are a subset of the captured NMR spin systems, and wherein the reference NMR spin systems belong to compounds which are omnipresent in the fluid class,
      wherein the model appliance is derived from a teaching database, the teaching database comprising for each of a plurality of teaching samples of the fluid class
         values of the captured characteristics, including values for the concentrations of the captured substances,
         and chemical shift values of the captured NMR spin systems, obtained through use of a teaching NMR spectrum recorded of the respective teaching sample and assignment of peaks in the teaching NMR spectrum to the captured NMR spin systems and determining the chemical shift values of the peaks,
      and wherein the model appliance is based on correlation functions for the chemical shift values and the captured characteristics;
   b) recording an NMR spectrum of the sample of the fluid class;
   c) identifying peaks in the recorded NMR spectrum which belong to the defined reference NMR spin systems of the model appliance, and determining experimental chemical shift values of the peaks from the recorded NMR spectrum; and
   aa') predicting chemical shift values of non-reference NMR spin systems of the captured NMR spin systems by applying the model appliance onto the experimental chemical shift values of the reference NMR spin systems;
   bb') calculating the concentration of the at least one substance by applying the model appliance onto the experimental chemical shift values of the reference NMR spin systems and the predicted chemical shift values of the non-reference NMR spin systems obtained in step aa'), by applying a 2F sub-model of full type which indicates the characteristics $x_j$ as a function f of the chemical shift values $\delta_l$ of the captured NMR spin systems, with $x_j=f_j(\delta_1, \ldots, \delta_S)$, with j: index of captured characteristics, with j=1, ..., C and C: number of captured characteristics, and with l: index of captured NMR spin systems, with l=1, ..., S and S: number of captured NMR spin systems.

22. A method according to claim 21, wherein the at least one substance, the concentration of which is determined by NMR spectroscopy, comprises an ion or other NMR inactive substance.

23. A method for determining the concentration of at least one compound contained in a sample of a fluid class comprising:
   a) providing a model appliance representing an information of correlation between captured characteristics of the fluid class, wherein the captured characteristics include concentrations of captured substances contained in the fluid class, and chemical shift values of captured NMR spin systems belonging to compounds contained in the fluid class, wherein the compounds are among the captured substances,
      wherein the model appliance comprises defined reference NMR spin systems, wherein the reference NMR spin systems are a subset of the captured NMR spin systems, and wherein the reference NMR spin systems belong to compounds which are omnipresent in the fluid class,
      wherein the model appliance is derived from a teaching database, the teaching database comprising for each of a plurality of teaching samples of the fluid class
         values of the captured characteristics, including values for the concentrations of the captured substances,
         and chemical shift values of the captured NMR spin systems, obtained through use of a teaching NMR spectrum recorded of the respective teaching sample and assignment of peaks in the teaching NMR spectrum to the captured NMR spin systems and determining the chemical shift values of the peaks,
      and wherein the model appliance is based on correlation functions for the chemical shift values and the captured characteristics;
   b) recording an NMR spectrum of the sample of the fluid class;
   c) identifying peaks in the recorded NMR spectrum which belong to the defined reference NMR spin systems of the model appliance, and determining experimental chemical shift values of the peaks from the recorded NMR spectrum; and
   aa") predicting a chemical shift value of at least one of the captured NMR spin systems, with the at least one NMR spin system belonging to the compound, by applying the model appliance onto the experimental chemical shift values of the reference NMR spin systems, wherein the at least one NMR spin system is a non-reference NMR spin system;
   bb") identifying at least one peak in the recorded NMR spectrum of the sample which belongs to the at least one NMR spin system though use of the predicted chemical shift value;
   cc") calculating the concentration of the compound based on the shape and/or size of the identified at least one peak in the recorded NMR spectrum of the sample.

24. The method according to claim 23, wherein in step cc"), the concentration of the compound is calculated through use of peak integration and/or lineshape fitting.

* * * * *